(12) United States Patent
Vilenchik et al.

(10) Patent No.: US 10,314,843 B2
(45) Date of Patent: Jun. 11, 2019

(54) COMBINATIONS FOR THE TREATMENT OF NEOPLASMS USING QUIESCENT CELL TARGETING AND INHIBITORS OF MITOSIS

(71) Applicant: Felicitex Therapeutics, Inc., Newton, MA (US)

(72) Inventors: Maria Vilenchik, Newton, MA (US); Michael Frid, Medford, MA (US); Alexandra Kuznetsova, Natick, MA (US); Yuriy Gankin, Newton, MA (US); Marc Duey, Chester Springs, PA (US)

(73) Assignee: Felicitex Therapeutics, Inc., Natick, MA (US)

( * ) Notice: Subject to any disclaimer, the term of this patent is extended or adjusted under 35 U.S.C. 154(b) by 0 days.

(21) Appl. No.: 15/488,143

(22) Filed: Apr. 14, 2017

(65) Prior Publication Data

US 2017/0296542 A1    Oct. 19, 2017

Related U.S. Application Data

(60) Provisional application No. 62/323,583, filed on Apr. 15, 2016.

(51) Int. Cl.
| | | |
|---|---|---|
| *A61K 31/519* | (2006.01) | |
| *A61K 31/337* | (2006.01) | |
| *A61K 31/475* | (2006.01) | |
| *A61K 31/496* | (2006.01) | |
| *A61K 45/06* | (2006.01) | |

(52) U.S. Cl.
CPC .......... *A61K 31/519* (2013.01); *A61K 31/337* (2013.01); *A61K 31/475* (2013.01); *A61K 31/496* (2013.01); *A61K 45/06* (2013.01)

(58) Field of Classification Search
CPC .. A61K 31/519; A61K 31/337; A61K 31/475; A61K 31/496; A61K 45/06
USPC .......................................................... 514/249
See application file for complete search history.

(56) References Cited

U.S. PATENT DOCUMENTS

| | | | | |
|---|---|---|---|---|
| 2014/0275064 A1* | 9/2014 | Leblond | ................ | C07C 271/28 514/232.8 |
| 2014/0371251 A1* | 12/2014 | Aberger | ................ | A61K 31/00 514/275 |
| 2015/0266825 A1 | 9/2015 | Hood et al. | | |
| 2015/0292032 A1 | 10/2015 | Vilenchik et al. | | |
| 2017/0296541 A1 | 10/2017 | Vilenchik et al. | | |

FOREIGN PATENT DOCUMENTS

WO    2016/055916 A1    4/2016

OTHER PUBLICATIONS

Friedman et al. Journal of Cellular Biochemistry 2007, 102 274-279.*
Ewton et al. Mol. Cancer Ther., 2011, 10(11), 2104-2114.*
American cancer society Jun. 6, 2016; https://www.cancer.org/treatment/treatments-and-side-effects/treatment-types/targeted-therapy/what-is.html (Year: 2016)*
Anderson el al. "The Dual Pathway Inhibitor Rigosertib Is Effective in Direct Patient Tumor Xenografts of Head and Neck Squamous Cell Carcinomas" Molecular Cancer Therapeutics. Jul. 19, 2013 (Jul. 19, 2013) vol. 12, p. 1994-2005.
Chaffer, C. L. et al., "A perspective on cancer cell metastasis," Science. Mar. 25, 2011;331(6024):1559-64. doi:10.1126/science. 1203543.
Coller et al., A new description of cellular quiescence, PLoS Biology, 2006, v. 4, e83.
Graybill et al. "Vintafolide: a novel targeted agent for epithelial ovarian cancer," Future Oncology, Mar. 2014, vol. 10, p. 541-548 (Only Abstract Provided ).
International Search Report and Written Opinion for Application No. PCT/US2017/027719, dated Jul. 21, 2017 (13 pages).
International Search Report and Written Opinion for Application No. PCT/US2017/027734, dated Jul. 21, 2017 (10 pages).
Jackson, R. C., "The problem of the quiescent cancer cell," Adv Enzyme Regul. 1989;29:27-46.
Karikios et al. "Irreversible EGFR inhibitors in advanced non-small-cell lung carcinoma: rationale and clinical evidence" Clinical Investigation. 2012, vol. 2, p. 317-325.
Lin et al. "Metabolism and Pharmacokinetics of Allitinib in Cancer Patients: The Roles of Cytochrome P450s and Epoxide Hydrolase in its Biotransformation," Drug Metabolism & Disposition, May 2014, v. 42, pp. 872-884.
Tyson et al. "Fractional proliferation: a method to deconvolve cell population dynamics from single-cell data," Nature Methods. Aug. 12, 2012 (Aug. 12, 2012) vol. 9, p. 923-928.

\* cited by examiner

*Primary Examiner* — Yevgeny Valenrod
(74) *Attorney, Agent, or Firm* — Nutter McClennen & Fish LLP

(57) ABSTRACT

The present invention provides compositions and methods for the treatment of neoplasms, in particular, by targeting of quiescent cancer cells with therapeutic agents in combination with other treatments effective against certain neoplastic conditions, in particular, anti-cancer treatment with therapeutic agents that are inhibitors of mitosis (a mitotic inhibitor).

20 Claims, 38 Drawing Sheets

COMBINATIONS FOR THE TREATMENT OF NEOPLASMS USING QUIESCENT CELL TARGETING AND INHIBITORS OF MITOSIS

BACKGROUND OF THE INVENTION

Cancer cell quiescence, effectively a cell in a state of sleep, has been recognized recently as a major mechanism of the resistance of cancer cells to treatments and for providing a pathway for disease recurrence. This quiescence, alternatively called cellular dormancy, is due to arrest at $G_0$ phase of the cell cycle. Typically, a cell enters a cell cycle from gap phase 1 ($G_1$), as shown in FIG. 1. After a synthesis phase (S) and a short pre-mitotic interval ($G_2$), the cell divides by mitosis (M) followed by a return to $G_1$. Instead of $G_1$, however, a cell can enter cellular dormancy or quiescence, designated as the $G_0$ phase. Cancer cells can either enter an irreversible state before undergoing terminal differentiation, termed senescence, or enter a reversible, true quiescent $G_0$ state from which they could resume cycling, like quiescent fibroblasts (Coller H A, Sang L, and Roberts J M (2006) A new description of cellular quiescence, *PLoS Biology* 4, e83).

A population of cells naturally may be in a quiescent state at any given time and remain quiescent for an indeterminate period until receipt of a signal to enter the cell division cycle. In one example, the proportion of cancer cells in quiescent state within a population in a tumor may be increased by environmental factors, such as lack of nutrients, hypoxia, high concentration of reactive oxygen species, etc. Cells may also be induced into the quiescent state by the action of a drug substance, as in pharmacological quiescence.

The energy and nutrient requirements of a quiescent cell are reduced relative to a dividing cell. Since current cancer therapies target dividing cells, as illustrated in FIG. 2, and therefore a cancer cell must be in the cell division cycle for such treatments to affect it. Accordingly, a quiescent cancer cell is resistant to treatments that affect one of more cellular proliferation processes by means of damaging exposed DNA, interfering with DNA replication or repair, interfering with mitosis, or other mechanisms.

Both anticancer therapeutics and radiation treatments produce adverse effects. Consequently, doses and duration of treatment are limited by toxicity and lower effective doses and/or shorter treatment durations are highly desirable. Upon reduction in doses or discontinuation of treatment, however, the surviving quiescent cancer cells can cause cancer recurrence upon re-entry to the cell cycle, the timing of which cannot be predicted. Further, metastatic cancer cells in the bloodstream may experience a period of quiescence while they adapt to their new microenvironment (Chaffer C L and Weinberg R A (2011) A perspective on cancer cell metastasis, *Science* 331, 1559-1564). Quiescent cancer cells degrade their polyribosomes, thus blocking translation and reducing total RNA and protein content. These shrunk cancer cells may be able to enter the bores of capillaries (approximately 8 μm diameter) whereas cycling cancer cells are usually much larger (20-30 μm).

Accordingly, the existence of a population of quiescent cancer cells within a neoplasm is recognized as an obstacle to successful and durable treatment (Jackson R C (1989) The problem of the quiescent cancer cell, *Advances in Enzyme Regulation* 29, 27-46). Evidence for resistance of quiescent cancer cells derived from various cancer types and to various anti-cancer treatments has been reported.

Yet, despite a growing appreciation of the importance of cancer cell quiescence, this issue remains unaddressed clinically. Accordingly, the present invention provides methods and combinations for the treatment of neoplasms that features the targeting of quiescent cancers cells by small molecules, particularly molecules effective against quiescent cancer cells, in combination with treatments known to be effective against certain neoplastic cells.

SUMMARY OF THE INVENTION

The present invention provides compositions and methods for the treatment of neoplasms, in particular, by targeting of quiescent cancer cells with therapeutic agents in combination with other treatments effective against certain neoplastic conditions, in particular, anti-cancer treatment with therapeutic agents that are inhibitors of mitosis (a mitotic inhibitor).

Generally, the invention features a method of treating a neoplasm comprising: administering to a subject in need thereof a therapeutically effective amount of (a) a therapeutic agent effective against quiescent cancer cells; and (b) second agent which is an inhibitor of mitosis, wherein the two agents can be administered sequentially or concomitantly. In some embodiments, the neoplasm is a cancer or a population of cancer cells in vitro or in vivo. In some embodiments, the subject receiving the treatment is diagnosed with cancer (e.g., metastatic or pre-metastatic). In some embodiments, the subject has been previously treated with a first-line therapy against cancer. In some embodiments, the subject is treated, or has been treated, with two or more inhibitors of mitosis sequentially or concomitantly.

In some embodiments, the combined treatment may result in improved outcomes, such as increased survival, reduction of severity, delay or elimination of recurrence, or reduced side effects of the primary treatments (i.e., the inhibitor of mitosis). In some embodiments, the second agent is administered at lower dose and/or for a shorter duration when administered as part of the combination as compared to a treatment with the agent alone. For example, in some embodiments, the $EC_{50}$ value of the inhibitor of mitosis is at least 20% lower in the combination treatment when compared to the same treatment with the inhibitor of mitosis alone, as determined, for example, in cell-based assays. In some embodiments, the combination treatment increases fraction of apoptotic cells in a treated population as compared to either agent alone, by at least by 2-fold as determined, for example, by fraction of sub-$G_0$ cells by FACS assay.

In one embodiment, the therapeutic agent effective against quiescent cancer cells is a DYRK1 inhibitor. In some embodiments, the DYRK1 inhibitor is a compound that inhibits activity of a DYRK1 kinase, either DYRK1A or DYRK1B (in vitro or in vivo), for example, with an $IC_{50}$ of 100 nM or lower in biochemical assays. In some embodiments, the DYRK1 inhibitor reduces the fraction of quiescent cancer cells (in vitro or in vivo) that would otherwise be found in the absence of such inhibitor, for example, by at least 10%. In some embodiments, the DYRK1 inhibitor inhibits both DYRK1A and DYRK1B. In some embodiments, the DYRK1 inhibitor is selective for DYRK1A or DYRK1B.

In one embodiment, the therapeutic agent effective against quiescent cancer cells is a DYRK1 inhibitor. In one embodiment, the DYRK1 inhibitor is a compound of formula I:

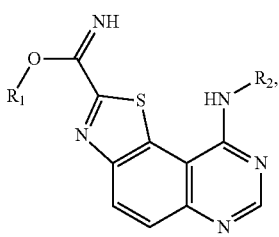

(I)

or a pharmaceutically acceptable salt or solvate thereof, wherein, $R_1$ is a substituted or unsubstituted $C_{1-8}$ alkyl, a substituted or unsubstituted phenyl, or a substituted or unsubstituted benzyl;

$R_2$ is phenyl, optionally substituted with up to four groups independently selected from halo, CN, $NO_2$, $NHC(O)C_{1-4}$ alkyl, $C_{1-4}$ alkyl, OH, $OC_{1-4}$ alkyl, wherein two adjacent groups and their intervening carbon atoms may form a 5- to 6-membered ring containing one or more heteroatoms selected from N, O, or S.

In one embodiment, the compound of formula I is selected from:

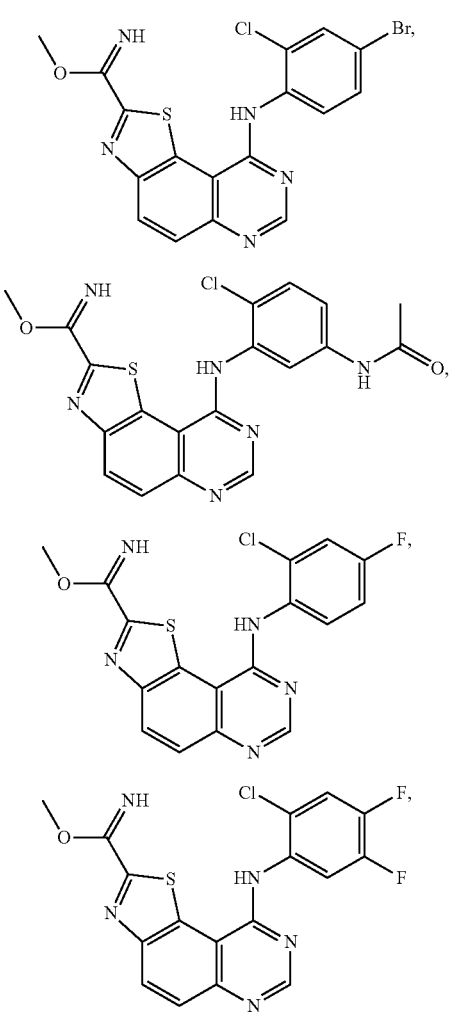

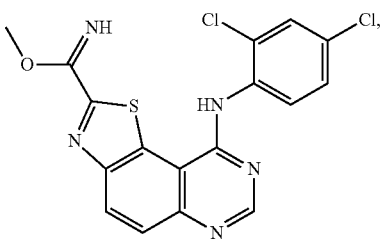

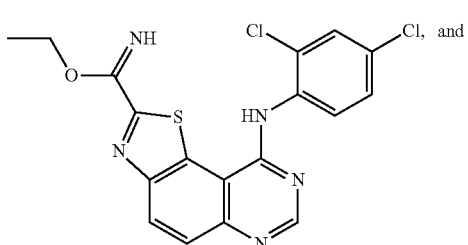

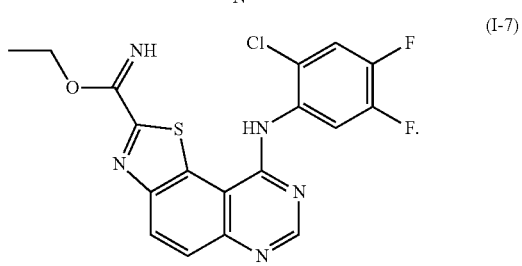

In another embodiment, the methods of the invention further provide (c) administering to the subject another cancer therapy, for example, radiation therapy or other cancer treatment.

In one embodiment, the methods of the invention comprise: administering to a subject in need thereof a therapeutically effective amount of (a) a therapeutic agent of formula I; (b) an inhibitor of mitosis; and (c) radiation therapy; each therapy being administered sequentially or concomitantly. For example, in some embodiments, the subject is first treated with radiation therapy, whereupon the subject is administered a therapeutic agent of Formula I, alone or in combination with the inhibitor of mitosis. In some embodiments, the subject is co-administered (a) the therapeutic agent effective against quiescent cancer cells, (b) the inhibitor of mitosis and, optionally, (c) the radiation therapy. In some embodiments, the inhibitor of mitosis is an inhibitor of mitosis effective to treat or prevent a neoplasm, including but not limited to, all such compounds approved for the treatment of cancer and compounds that otherwise demonstrate efficacy in treating cancer in mammalian subject (e.g., mice, rats, dogs, monkeys, humans), and compounds that demonstrate efficacy against neoplastic cells in vitro. Many such compounds are known.

In one embodiment, the inhibitor of mitosis is a taxane. In a further embodiment, the taxane inhibitor of mitosis is, for example, BMS-188796, BMS-188797, cabazitaxel, DEP cabazitaxel, docetaxel, larotaxel (XRP9881, RPR109881), paclitaxel, taxoprexin (DHA-paclitaxel), and tesetaxel (DJ-927).

In another embodiment, the inhibitor of mitosis is a vinca alkaloid. In a further embodiment, the vinca alkaloid inhibitor of mitosis is, for example, vinblastine, vincristine, vindesine, vinflunine, and vinorelbine. In another embodiment, the vinca alkaloid inhibitor of mitosis is vintafolide.

In another embodiment, the inhibitor of mitosis is a PLK1 inhibitor. In a further embodiment, the PLK1 inhibitor of mitosis is, for example, BI-2536, GSK 461364, GW843682X, HMN-214 and HMN-176, MLN-0905, NMS-P937, rigosertib, Ro3280, SBE 13, and volasertib. In a further embodiment, the inhibitor of mitosis is BI-2536 or GSK461364.

In another embodiment, the neoplasm being treated is a cancer, for example, biliary cancer, brain cancer, breast cancer, cervical cancer, colon cancer, gastric cancer, kidney cancer, head and neck cancer, leukemia, liver cancer, lung cancer, lymphoma, ovarian cancer, pancreatic cancer, prostate cancer, rectal cancer, sarcoma, skin cancer (e.g. melanoma), testicular cancer, thyroid cancer, or uterine cancer. In a further embodiment, the neoplasm being treated is a bladder cancer, breast cancer, colorectal cancer, non-small cell lung cancer, small cell lung cancer, ovarian cancer, and prostate cancer. In further embodiments, the cancer is primary or metastatic. In yet further embodiments, the cancer is of the type represented by the cell line types shown in the Examples.

The embodiments are not meant to be limiting with regard to additional combination components, especially therapeutic agents and inhibitors that are part of existing treatment combinations, such as, for example, TPF wherein T stands for Taxotere®, that is docetaxel, or PCV wherein V stands for vincristine sulfate. Similarly, the embodiments are not meant to be limiting with regard to routes and order of administration or with regard to patient type (previously untreated or previously treated, absence or presence of co-morbid conditions, sex, etc.) or stage of patient's disease, type of inhibitor of mitosis, etc.

µM Compound I-7; Panel D: FBS+ media with 2 nM paclitaxel; Panel E: FBS+ media with 4 µM Compound I-7 and 2 nM paclitaxel.

Figure 35:
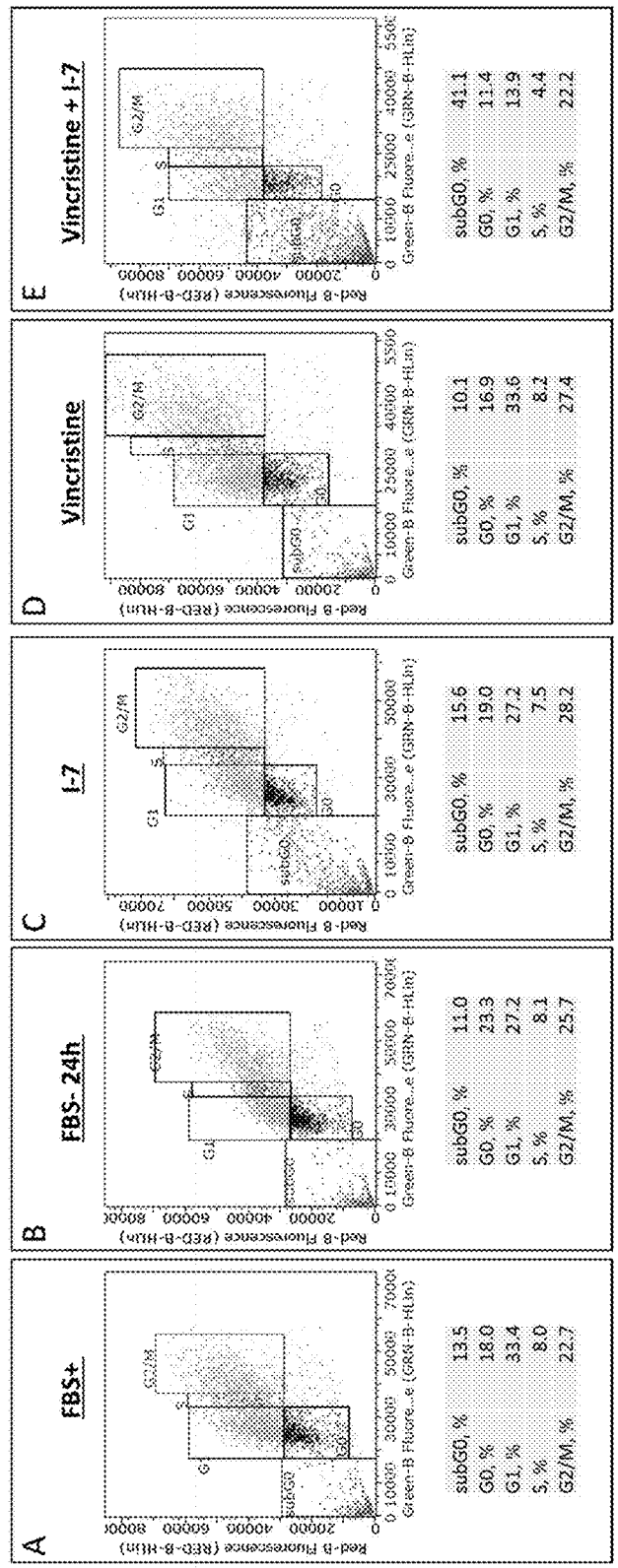

FIG. 35 shows FACS analyses of cell cycle distribution of DMS273 cells incubated for 24 hours in Panel A: FBS+ media; Panel B: FBS− media; Panel C: FBS+ media with 4 µM Compound I-7; Panel D: FBS+ media with 1.1 nM vincristine; Panel E: FBS+ media with 4 µM Compound I-7 and 1.1 nM vincristine.

Figure 36:
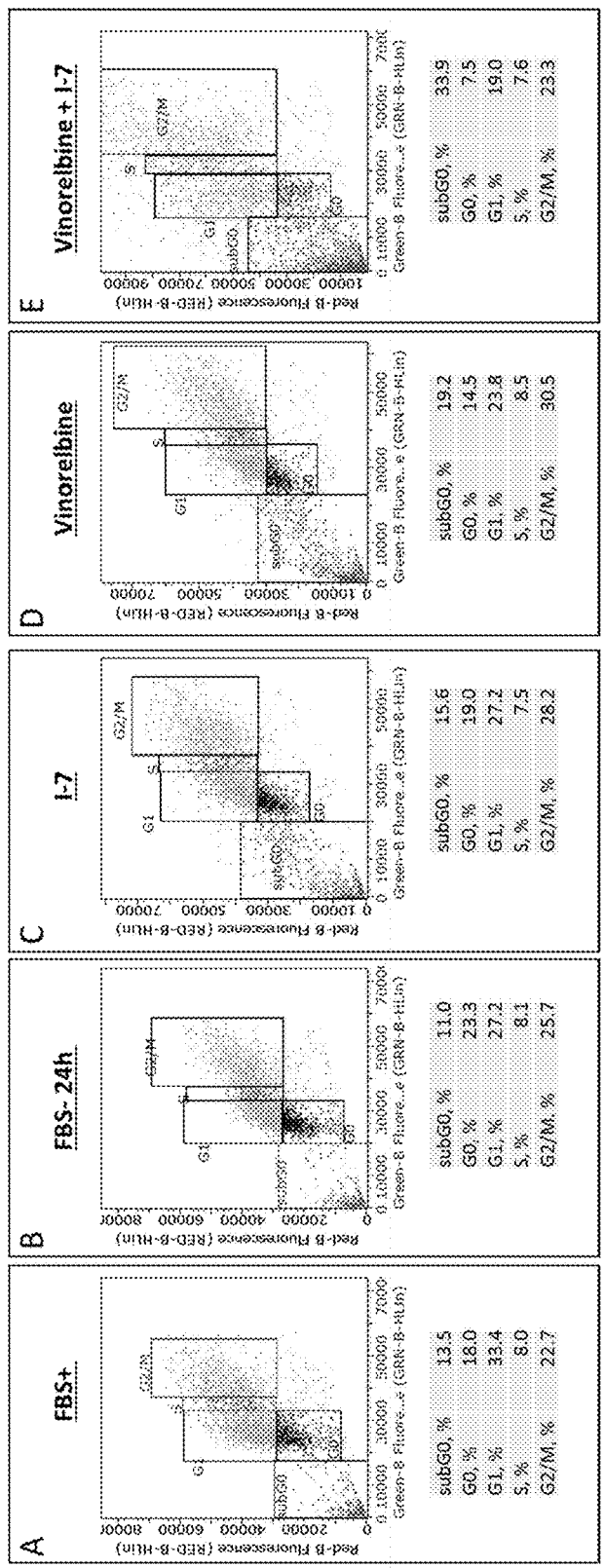

FIG. 36 shows FACS analyses of cell cycle distribution of DMS273 cells incubated for 24 hours in Panel A: FBS+ media; Panel B: FBS− media; Panel C: FBS+ media with 4 µM Compound I-7; Panel D: FBS+ media with 8.1 nM vinorelbine; Panel E: FBS+ media with 4 µM Compound I-7 and 8.1 nM vinorelbine.

Figure 37:
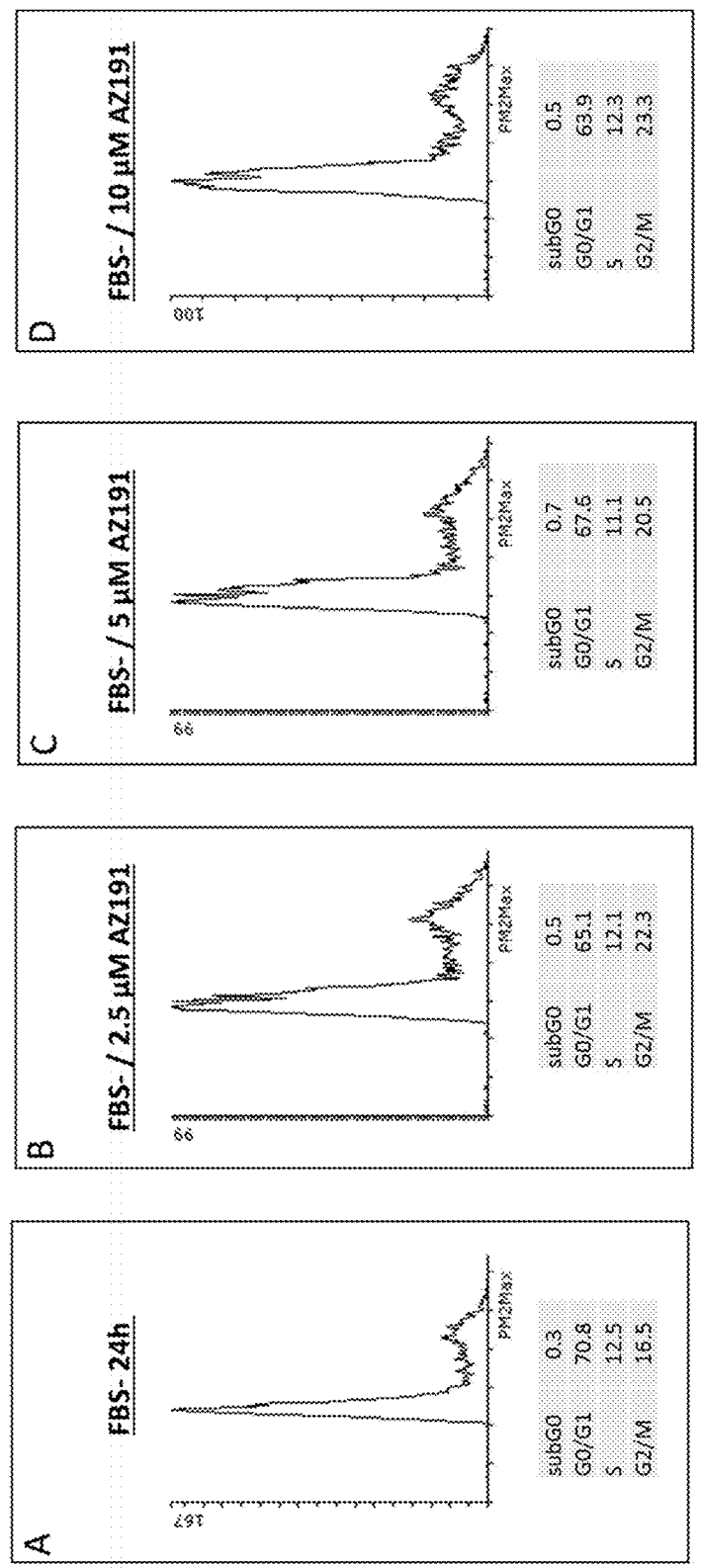

FIG. 37 FACS analyses by DNA content of cell cycle distribution of SW620 cells. The cells were incubated in Panel A: 24 hours in FBS− media; Panel B: 24 hours in FBS-media with 2.5 µM AZ191; Panel C: 24 hours in FBS− media with 5 µM AZ191; Panel D: 24 hours in FBS− media with 10 µM AZ191.

Figure 38:
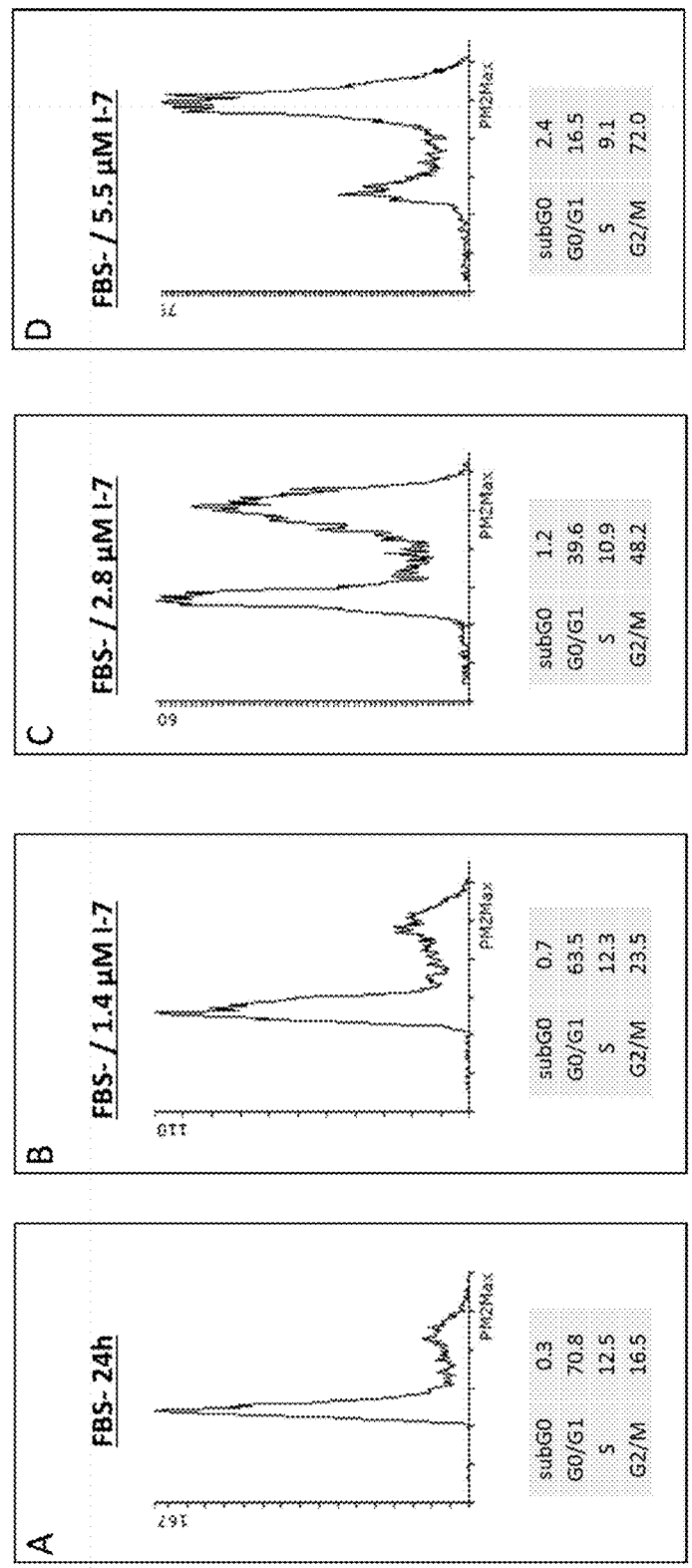

FIG. 38 shows FACS analyses by DNA content of cell cycle distribution of SW620 cells. The cells were incubated in Panel A: 24 hours in FBS− media with DMSO control; Panel B: 24 hours in FBS− media with 1.25 µM Compound I-7; Panel C: 24 hours in FBS-media 2.5 µM Compound I-7; Panel D: 24 hours in FBS− media with 5 µM Compound I-7.

DETAILED DESCRIPTION OF THE INVENTION

Glossary

In the present invention, an "alkyl" group is a saturated, straight or branched, hydrocarbon group, comprising from 1 to 8 carbon atoms ($C_{1-8}$ alkyl group), in particular from 1 to 6, or from 1 to 4 carbons atoms, unless otherwise indicated. Examples of alkyl groups having from 1 to 6 carbon atoms inclusive are methyl, ethyl, propyl (e.g., n-propyl, iso-propyl), butyl (e.g., tert-butyl, sec-butyl, n-butyl), pentyl (e.g., neo-pentyl), hexyl (e.g., n-hexyl), 2-methylbutyl, 2-methylpentyl and the other isomeric forms thereof. Alkyl groups may be unsubstituted or substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "alkenyl" group is a straight or branched hydrocarbon group comprising at least one double carbon-carbon bond, comprising from 2 to 8 carbon atoms (unless otherwise indicated). Examples of alkenyl groups containing from 2 to 6 carbon atoms are vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof. Alkenyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "alkynyl" group is a straight or branched hydrocarbon group comprising at least one triple carbon-carbon bond, comprising from 2 to 8 carbon atoms. Alkynyl groups may be substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "aryl" group is an aromatic hydrocarbon cycle, comprising from 5 to 14 carbon atoms. Most preferred aryl groups are mono- or bi-cyclic and comprises from 6 to 14 carbon atoms, such as phenyl, alpha-naphtyl, 3-naphtyl, antracenyl, preferably phenyl. "Aryl" groups also include bicycles or tricycles comprising an aryl cycle fused to at least another aryl, heteroaryl, cycloalkyl or heterocycloalkyl group, such as benzodioxolane, benzodioxane, dihydrobenzofurane or benzimidazole. Aryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro, and amino groups. In addition, aryl groups may be substituted by adjacent substituents which can, taken together with the carbon atom to which they are attached, form a 5- to 6-membered ring which may contain one or more heteroatom(s) selected from N, O, and S.

In the present invention, a "halogen atom" or "halo" is a Cl, Br, F, or I atom.

In the present invention, an "alkoxyl" group is an alkyl group linked to the rest of the molecule through an oxygen atom, of the formula O-alkyl.

In the present invention, an "amino" group is a $NH_2$, NH-alkyl, or $N(alkyl)_2$ group.

In the present invention, a "heteroaryl" group is an aryl group whose cycle is interrupted by at least at least one heteroatom, for example a N, O, or S, atom, such as thiophene or pyridine. Heteroaryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, heteroaryl groups may be substituted by adjacent substituents which can, taken together with the carbon atom to which they are attached, form a 5- to 6-membered ring which may contain one or more heteroatom(s) selected from N, O, and S.

In the present invention, a "cycloalkyl" denotes a saturated alkyl group that forms one cycle having preferably from 3 to 14 carbon atoms, and more preferably 3 to 8 carbon atoms, such as cyclopropyl, cyclobutyl, cyclopentyl, cyclohexyl, cycloheptyl, and cyclooctyl. Cycloalkyl groups may be unsubstituted or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro, and amino groups. In addition, cycloalkyl groups may be substituted by adjacent substituents which can, taken together with the carbon atom to which they are attached, form a 5- to 6-membered ring which may contain one or more heteroatom(s) selected from N, O, and S.

In the present invention, a "heterocycloalkyl" group is a cycloalkyl group comprising at least one heteroatom, such as pyrrolidine, tetrahydrothiophene, tetrahydrofuran, piperidine, pyran, dioxin, morpholine or piperazine. A heterocycloalkyl group may in particular comprise from four to fourteen carbon atoms, such as morpholinyl, piperidinyl, pyrrolidinyl, tetrahydropyranyl, dithiolanyl. Heterocycloalkyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro and amino groups. In addition, heterocycloalkyl groups may be substituted by adjacent substituents which can, taken together with the carbon atom to which they are attached, form a 5- to 6-membered ring which may contain one or more heteroatom(s) selected from N, O, and S.

As used herein, a "neoplasm" means an abnormal mass of tissue that results from neoplasia. "Neoplasia" means a process of an abnormal proliferation of cells. In some embodiments of the invention, a neoplasm is a solid cancer, or alternately a hematopoietic cancer. The neoplasia may be benign, pre-malignant, or malignant. The term neoplasm encompasses mammalian cancers, in some embodiments, human cancers, and carcinomas, sarcomas, blastomas of any tissue (for example adenocarcinomas, squamous cell carcinoma, osteosarcomas, etc.), germ cell tumors, glial cell tumors, lymphomas, leukemias, including solid and lymphoid cancers, kidney, breast, lung, bladder, colon, ovarian, prostate, rectal, pancreatic, stomach, brain, head and neck, skin, uterine, cervical, testicular, esophagus, thyroid, biliary cancer, liver cancer, and cancer of the bone and cartilaginous tissue, including non-Hodgkin's lymphomas (e.g., Burkitt's, Small Cell, and Large Cell lymphomas) and Hodgkin's lymphoma, leukemia, multiple myeloma, and myelodysplastic syndrome.

As used herein, the terms "treat," "treating," or "treatment," mean to counteract a medical condition (e.g., cancer) to the extent that the medical condition is improved according to a clinically-acceptable standard. Improvement in cancer can include: 1) reduced rate of tumor growth (tumor growth inhibition), 2) tumor shrinkage (regression), 3) remission, whether partial or total, 4) reduction in metastases, 5) prolonging progression free survival, and 6) delay or elimination of recurrence. In certain embodiments of the invention, treating includes achieving, partially or substantially, one or more of the following results: partially or totally reducing the cancer mass, or volume, or the malignant cell count; ameliorating or improving a clinical symptom or indicator associated with solid cancers or hematopoietic cancers; delaying, inhibiting, or preventing the progression of solid cancers or hematopoietic cancers; or partially or totally delaying, inhibiting or preventing the onset or development of solid cancers or hematopoietic cancers. "Treatment" also can mean prolonging survival compared to expected survival without treatment or compared to standard of care treatment.

Treating includes prophylactic or preventative treatment. "Prophylactic treatment" refers to treatment before appearance or re-appearance of clinical symptoms of a target disorder to prevent, inhibit, or reduce its occurrence, severity, or progression.

As used herein, an "effective amount" refers to an amount of a therapeutic agent or a combination of therapeutic agents that is therapeutically or prophylactically sufficient to affect the desired improvement in the targeted disorder. Examples of effective amounts typically range from about 0.0001 mg/kg of body weight to about 500 mg/kg of body weight per single administered dose, such doses being administered once or over a period of time. An example range is from about 0.0001 mg/kg of body weight to about 5 mg/kg per dose. In other examples, the range can be from about 0.0001 mg/kg to about 5 mg/kg per single administered dose. In still other examples, effective amounts range from about 0.01 mg/kg of body weight to 50 mg/kg of body weight per single administered dose, or from 0.01 mg/kg of body weight to 0.1 mg/kg, 0.5 mg/kg, 1 mg/kg, 2 mg/kg, 3 mg/kg, 4 mg/kg, 5 mg/kg, 6 mg/kg, 10 mg/kg, 20 mg/kg, 25 mg/kg, 30 mg/kg, or 40 mg/kg of body weight per single administered dose. For agents of known clinical use, an example of an effective dose is that amount approved of by a regulatory agency for treatment of an indication.

As used herein, the term "subject" refers to a mammal, for example a human, but can also mean an animal in need of veterinary treatment, e.g., companion animals (e.g., dogs, cats, and the like), farm animals (e.g., cows, sheep, pigs, horses, and the like), and laboratory animals (e.g., rats, mice, guinea pigs, and the like).

As used herein, the term "therapeutic agent" means any chemical molecule used or contemplated for use or investigated for use in cancer treatment, including cytotoxic, cytostatic, or targeted agents, whether small molecules, or peptides, or antibodies, or oligonucleotides, irrespective of mechanism of action. As used herein, the terms "therapeutic" or "therapeutic agent" refer to either the active pharmaceutical ingredient (API) or its pharmaceutically acceptable salt or hydrate (solvate), or a drug product containing the therapeutic agent, however formulated, and whether API is amorphous or crystalline and of whatever polymorphic form. Formulation means a combination of an active pharmaceutical ingredient (API, drug substance) or ingredients (APIs) combined with excipients and/or delivery vehicle to make an administrable dosage form (drug product). For example, as used herein, a reference to paclitaxel includes Taxol®, Abraxane®, Lipusu®, and any other drug product with paclitaxel as the active ingredient.

The therapeutic agents of the invention can be administered alone, but are generally administered with a pharmaceutically acceptable carrier, with respect to standard pharmaceutical practice (such as described in Remington's Pharmaceutical Sciences, Mack Publishing). Accordingly, a further object of this invention relates to pharmaceutical compositions defined herein and pharmaceutically acceptable carriers.

As used herein, the term "inhibitor" means any composition that reduces the activity of an enzyme. An example of an inhibitor is a chemical molecule. A measure of the potency of an inhibitor is its "50% inhibitory concentration" ($IC_{50}$). $IC_{50}$ concentration or $IC_{50}$ value is the concentration of an inhibitor at which 50% of the enzymatic activity is inhibited by the inhibitor. Methods for the determination of $IC_{50}$ values, for example, of kinase inhibitors are known to persons of ordinary skill in the art and include direct and indirect functional assays, such as the HotSpot™ kinase assay technology (Reaction Biology Corporation, Malvern, Pa., www.reactionbiology.com) or competition binding assays, such as KINOMEscan® (DiscoverX Corporation, Freemont, Calif., www.discoverx.com).

A measure of the potency of a therapeutic agent against a cell line is its "50% effective concentration" ($EC_{50}$). $EC_{50}$ concentration or $EC_{50}$ value is the concentration of a drug that produces half-maximal response, such as, for example, 50% growth inhibition or 50% reduction in cell viability. Methods for the determination of $EC_{50}$ values, for example, of kinase inhibitors are known to persons of ordinary skill in the art.

As used herein, the term "quiescence" or "quiescent state" refers to the $G_0$ state of the cell cycle, as understood by the practitioners of the art.

As used herein, the term "therapeutic agent effective against quiescent cancer cells" refers to a molecule that either reduces the fraction of quiescent cancer cells in a cell population or prevents, completely or substantially, an increase in fraction of quiescent cancer cells in a cell population under conditions that otherwise would lead to such an increase.

A "quiescent neoplastic cell", alternately referred to as a "quiescent cancer cell" means a cancer cell that exists in the quiescent, or $G_0$, state of the cell cycle. A "fraction of quiescent neoplastic cells" or "fraction of quiescent cancer cells", as used herein, means the portion of a cancer cell population that exists in the $G_0$ state of the cell cycle. Determining the fraction of quiescent neoplastic cells includes characterizing a cell population by distribution of its constituent cells within the stages of the cell cycle. The fraction of cells in the $G_0$ state (i.e., quiescent neoplastic cells) is quantified relative to the total cell population. The fraction may be expressed as a percentage of the total cell population (i.e. (number of quiescent cells divided by total cells in cell population) multiplied by 100). Characterization of the cell population by distribution of its constituent cells within the stages of the cell cycle may be achieved by techniques known to persons of ordinary skill in the art, and may include analysis by DNA and/or RNA content using flow cytometry methods, for example, fluorescence-activated cell sorting (FACS).

DETAILED DESCRIPTION

The present invention provides compositions and methods for the treatment of neoplasms, in particular, by targeting of quiescent cancers cells with therapeutic agents in combination with other treatments effective against certain neoplastic conditions, in particular, anti-cancer treatment with therapeutic agents which are inhibitors of mitosis.

Generally, the invention features a method of treating a neoplasm comprising: administering to a subject in need thereof a therapeutically effective amount of (a) a therapeutic agent effective against quiescent cancer cells; and (b) second agent which is an inhibitor of mitosis, wherein the two agents can be administered sequentially or concomitantly. In some embodiments, the neoplasm is a cancer or a population of cancer cells in vitro or in vivo. In some embodiments, the subject receiving the treatment is diagnosed with cancer (e.g., metastatic or pre-metastatic). In some embodiments, the subject has been treated previously with a first-line therapy against cancer. In some embodiments, the subject has been treated previously with second-line and/or other therapies. In some embodiments, the subject is treated, or has been treated, with radiation therapy. In some embodiments, the subject was treated with surgery, for example to resect or de-bulk a tumor. In other embodiments, the subject's neoplasm has recurred. In some embodiments, the subject is treated, or has been treated, with two or more inhibitor of mitosis sequentially or concomitantly.

In some embodiments, the combined treatment may result in improved outcomes, such as increased survival, reduction of severity, delay or elimination of recurrence, or reduced side effects of the primary treatments (i.e., the inhibitor of mitosis). In some embodiments, the second agent is administered at lower dose and/or for a shorter duration when administered as part of the combination as compared to a treatment with the agent alone. For example, in some embodiments, the $EC_{50}$ value of the inhibitor of mitosis is at least 20%, 25%, 30%, 40%, 50%, 100%, 3-fold, 5-fold, 10-fold lower in the combination treatment when compared to the same treatment with the first agent, as determined, for example, in cell-based assays. In some embodiments, the combination treatment increases fraction of apoptotic cells in a treated population as compared to either agent alone, by at least by 2-fold, 3-fold, 4-fold, 5-fold as determined, for example, by fraction of sub-$G_0$ phase cells in a FACS assay.

In one embodiment, the therapeutic agent effective against quiescent cancer cells is a DYRK1 inhibitor. In some embodiments, the DYRK1 inhibitor is a compound that inhibits activity of a DYRK1 kinase, either DYRK1A or DYRK1B (in vitro or in vivo), for example, with an $IC_{50}$ value of <100 nM, <90 nM, <80 nM, <70 nM, <60 nM, <50 nM, <40 nM, <30 nM, <20 nM, <10 nM, <5 nM or lower in biochemical assays. In some embodiments, the DYRK1 inhibitor reduces the fraction of quiescent cancer cells (in vitro or in vivo) in a population or a tumor that would otherwise be found in the absence of such inhibitor, for example, by at least 5%, 10%, 15%, 20%, 25%, 30%, 40%, 50% or more.

In some embodiments, the DYRK1 inhibitor inhibits both DYRK1A and DYRK1B. In some embodiments, the DYRK1 inhibitor is selective for DYRK1A, with ratio of DYRK1B $IC_{50}$ to DYRK1A $IC_{50}$ of 1000, 100, 50, 25, 10 to 1. In some embodiments, the DYRK1 inhibitor is selective for DYRK1B, with ratio of DYRK1A $IC_{50}$ to DYRK1B $IC_{50}$ of 1000, 100, 50, 25, 10, or 5 to 1. In some embodiments, the DYRK1 inhibitor is selective for DYRK1 by at least 4-fold, 5-fold, 10-fold, 20-fold, 50-fold, 100-fold as compared to DYRK2 and/or DYRK3 and/or DYRK4, as determined by ratios of $IC_{50}$ values. In some embodiments, the DYRK1 inhibitor is selective for DYRK1 by at least 4-fold, 5-fold, 10-fold, 20-fold, 50-fold, 100-fold, 500-fold, 1000-fold as compared to cyclin dependent kinases (CDKs) such, as for example, CDK2, as determined by ratios of $IC_{50}$ values.

Examples of known DYRK1 inhibitors include AZ191, DYRKi, harmine, ID-8, leucettine L41, NCGC00185981, INDY, ProINDY, TC-S 7004, and TG003. At least one known DYRK1 inhibitor, TC-S 7004, (US20120184562) is reported to be effective against quiescent cancer cells in vitro (Ewton D Z, Hu J, Vilenchik M, Deng X, Luk K C, Polonskaia A, Hoffman A F, Zipf K, Boylan J F, and Friedman E A. (2011) Inactivation of MIRK/DYRK1B kinase targets quiescent pancreatic cancer cells. Molecular Cancer Therapeutics 10: 2104-2114).

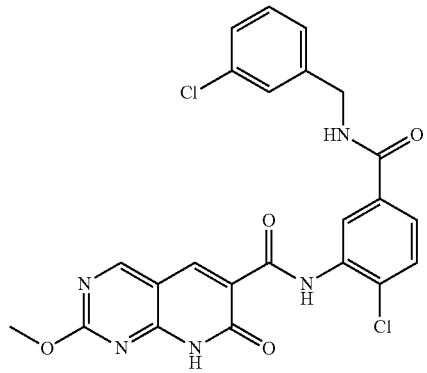

(TC-S 7004)

In one embodiment, the DYRK1 inhibitor is a compound of formula I:

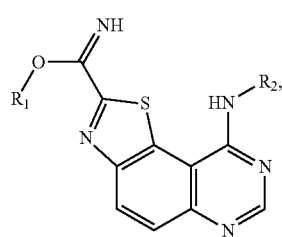

(I)

or a pharmaceutically acceptable salt or solvate thereof, wherein, $R_1$ is a substituted or unsubstituted $C_{1-8}$ alkyl, a substituted or unsubstituted phenyl, or a substituted or unsubstituted benzyl;

$R_2$ is phenyl, optionally substituted with up to four groups independently selected from halo, CN, $NO_2$, $NHC(O)C_{1-4}$ alkyl, $C_{1-4}$ alkyl, OH, $OC_{1-4}$ alkyl, wherein two adjacent groups and their intervening carbon atoms may form a 5- to 6-membered ring containing one or more heteroatoms selected from N, O, or S.

In one embodiment, the compound of formula I is selected from:

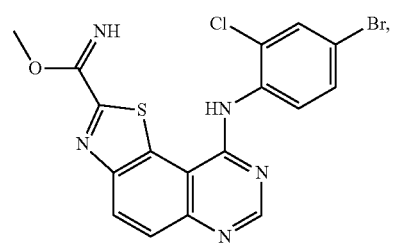
(I-1)

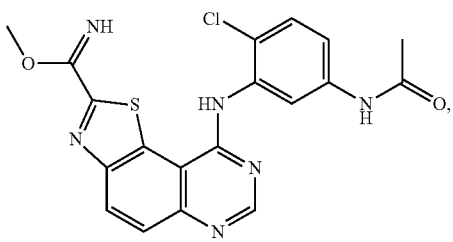
(I-2)

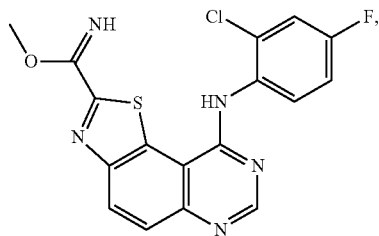
(I-3)

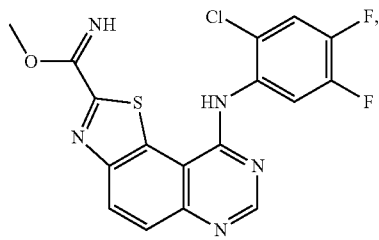
(I-4)

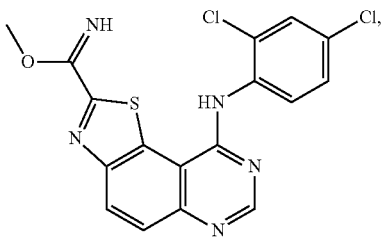
(I-5)

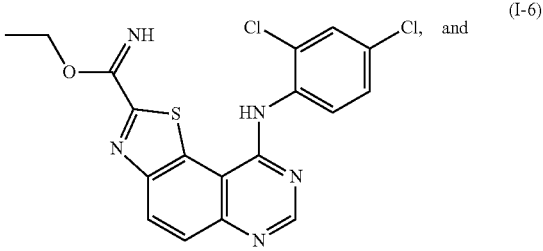
(I-6)

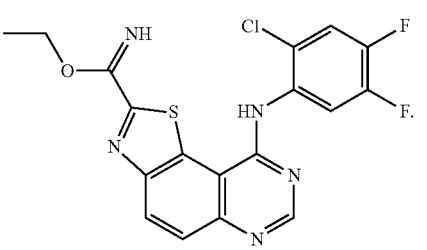
(I-7)

In another embodiment, the methods of the invention further provide (c) administering to the subject another cancer therapy, for example, radiation therapy or other cancer treatment.

In one embodiment, the methods of the invention comprise: administering to a subject in need thereof a therapeutically effective amount of (a) a therapeutic agent of formula I; (b) an inhibitor of mitosis; and (c) radiation therapy; each therapy being administered sequentially or concomitantly. For example, in some embodiments, the subject is first treated with radiation therapy, whereupon the subject is administered a therapeutic agent of Formula I, alone or in combination with the inhibitor of mitosis. In some embodiments, the subject is co-administered (a) the therapeutic agent effective against quiescent cancer cells, (b) the inhibitor of mitosis, and, optionally (c) the radiation therapy.

In some embodiments, the inhibitor of mitosis is an inhibitor of mitosis effective to treat or prevent a neoplasm, including but not limited to, all such compounds approved for the treatment of cancer, compounds in clinical trials for the treatment of cancer, compounds that otherwise demonstrate efficacy in treating cancer in mammalian subject (e.g., mouse, rats, monkeys, humans), and compounds that demonstrate efficacy against neoplastic cells in vitro. Many such compounds are known.

In one embodiment, the inhibitor of mitosis is a taxane. Taxanes useful for the methods of the invention include BMS-188796, BMS-188797, cabazitaxel, DEP cabazitaxel, docetaxel, larotaxel (XRP9881, RPR109881), paclitaxel, taxoprexin (DHA-paclitaxel), and tesetaxel (DJ-927).

In another embodiment, the inhibitor of mitosis is a vinca alkaloid. Vinca alkaloids useful for the methods of the invention include vinblastine, vincristine, vindesine, vinflunine, and vinorelbine. In another embodiment, the vinca alkaloid inhibitor of mitosis is vintafolide.

In another embodiment, the inhibitor of mitosis is a PLK1 inhibitor. PLK1 inhibitors useful for the methods of the invention include BI-2536, GSK461364, GW843682X, HMN-214 and HMN-176, MLN-0905, NMS-P937, rigosertib, Ro3280, SBE 13, and volasertib. In a further embodiment, the inhibitor of mitosis is BI-2536 or GSK461364.

In another embodiment, a neoplasm is biliary cancer, brain cancer, breast cancer, cervical cancer, colon cancer, gastric cancer, head and neck cancer, kidney cancer, leukemia, liver cancer, non-small cell lung cancer, small cell lung cancer, lymphoma, ovarian cancer, pancreatic cancer, prostate cancer, rectal cancer, sarcoma, skin cancer (e.g. melanoma), testicular cancer, thyroid cancer, or uterine cancer. In a further embodiment, the neoplasm is selected from bladder cancer, breast cancer, colorectal cancer, non-small cell lung cancer, small cell lung cancer, ovarian cancer, and prostate cancer. In further embodiments, the cancer is primary or metastatic. In yet further embodiments, the cancer is of the type represented by the cell line types shown in the Examples.

The embodiments are not meant to be limiting with regard to additional combination components, especially compounds that are part of existing treatment combinations, such as, for example, TPF wherein T stands for Taxotere®, that is docetaxel, or PCV wherein V stands for vincristine sulfate. The embodiments described here are illustrative and are not meant to be limiting with regard to routes and order of administration, patient type (previously untreated or previously treated, absence or presence of co-morbid conditions, age, sex, etc.), or stage of patient's disease, type of inhibitor of mitosis, etc.

Inhibitors of mitosis are known in the art (Dominguez-Brauer C, et al, (2015) Targeting mitosis in cancer: emerging strategies, *Molecular Cell* 60, 524-536). As used herein, the terms "inhibitor of mitosis" and "mitotic inhibitor" are equivalent and may be used interchangeably. An inhibitor of mitosis interrupts cell cycling during the M phase or at a checkpoint entering (the $G_2/M$ checkpoint) or leaving (the post-mitotic checkpoint) the M phase. In M phase, the chromosomes and cytoplasm are divided into two daughter cells (cytokinesis). Mitosis proceeds in five phases: prophase, prometaphase, metaphase, anaphase, and telophase and an inhibitor of mitosis can interrupt any of these phases. Examples inhibitors of mitosis include taxanes, vinca alkaloids, and PLK1 inhibitors.

For example, taxanes include BMS-188796, BMS-188797, cabazitaxel, DEP cabazitaxel, docetaxel, larotaxel (XRP9881, RPR109881), paclitaxel, taxoprexin (DHA-paclitaxel), and tesetaxel (DJ-927); vinca alkaloids include vincristine, vinblastine, vindesine, vinflunine, and vinorelbine; PLK1 inhibitors include BI-2536, GSK461364, GW843682X, HMN-214 and HMN-176, MLN-0905, NMS-P937, rigosertib, Ro3280, SBE 13, and volasertib.

A $G_0$ state is maintained by a specific program of gene expression. DYRK1 kinases, such as DYRK1A and DYRK1B, may be important for the maintenance of cancer cells in $G_0$ state (quiescent state).

DYRK1B/Mirk is a member of the Minibrain/DYRK family of kinases which mediates survival and differentiation in certain normal tissues. (Kentrup H, Becker W, Heukelbach J, Wilmes A, Schurmann A, Huppertz C, Kainulainen H, and Joost H G (1996) Dyrk, a dual specificity protein kinase with unique structural features whose activity is dependent on tyrosine residues between subdomains VII and VIII, *Journal of Biological Chemistry* 271, 3488-3495; Becker W, Weber Y, Wetzel K, Eirmbter K, Tejedor F J, and Joost H G (1998) Sequence characteristics, subcellular localization, and substrate specificity of DYRK-related kinases, a novel family of dual specificity protein kinases, *Journal of Biological Chemistry* 273, 25893-25902). DYRK1B is expressed at detectable levels in skeletal muscle cells and testes. Knockout of DYRK1B caused no evident abnormal phenotype in mice even in developing muscle, suggesting that DYRK1B is not an essential gene for normal development. Supporting this interpretation, normal fibroblasts exhibited no alteration in survival after 20-fold depletion of DYRK1B kinase levels. Thus, DYRK1B does not appear to be an essential gene for survival of normal cells yet there is evidence that it is upregulated in certain malignant cancer cells in which DYRK1B is believed to mediate survival by retaining cancer cells in quiescent state. These unusual characteristics suggest that DYRK1B may be an attractive target for therapeutic intervention and in particular for anti-cancer therapy directly against quiescent cancer cells.

The disclosed combinations and methods may afford one or more of the improvements as defined in the Glossary relative to the use of each individual components or existing single and combination treatments. Also, the disclosed combinations and methods may permit reduction in doses and/or frequency of administration of therapeutic agents and radiation to achieve the same improvements as a result of treatment relative to what is possible using individual components or existing single and combination treatments.

The disclosed combinations need not be synergistic to yield a significant improvement in the effectiveness of treatment relative to single therapy with an inhibitor of mitosis. As discussed above, quiescent cancer cells are inherently less susceptible to anti-cancer therapeutics, including mitotic inhibitors, and even a small fraction of quiescent cells that survives post treatment can lead to recurrence. Consequently, eradicating the resistant, quiescent cell populations in a neoplasm may or may not yield a synergistic reduction in $EC_{50}$ values yet may yield a significant improvement in cancer recurrence and appearance of metastatic neoplasms.

The administration regimen and routes of administration of the disclosed combinations may well vary depending on the neoplasm treated, extent of progression of the neoplasm, exact combination selected, age, sex, and physical condition of the subject, and other factors. Administration regimen may include multiple doses per period of time, the treatments administered concurrently or sequentially, etc. Furthermore, the combinations may be administered to subjects who are naive to treatment (have not been treated), or subjects who underwent previous treatments, or have undergone surgical resection or debulking of a solid tumor, or subjects whose cancers relapsed. For example, therapeutic agent effective against quiescent cancer cells may be administered before the inhibitor of mitosis. The therapeutic agent effective against quiescent cancer cells may be administered 6 hours, 12 hours, 24 hours, 48 hours, 72 hours, 96 hours, one week before the inhibitor of mitosis. The therapeutic agent effective against quiescent cancer cells may be administered at the same time (concomitantly) as the inhibitor of mitosis. The therapeutic agent effective against quiescent cancer cells may be administered 6 hours, 12 hours, 24 hours, 48 hours, 72 hours, 96 hours after the inhibitor of mitosis. The therapeutic agent effective against quiescent cancer cells and/or the inhibitor of mitosis may be administered before, after, or concomitantly with radiation or other therapy.

The therapeutic agent effective against quiescent cancer cells may be administered daily, every two days, every three days, every four days, once weekly, once every two weeks, once per month by oral, intravenous (IV), intraperitoneal (IP), subcutaneous (SC), intratumoral (IT), intrathecal, or other routes of administration.

The combinations may be administered to subjects who are naive to treatment (have not been treated), or subjects who underwent previous treatments with first-line, second-line, third-line, or other therapies, radiation treatments, or have undergone surgical resection or debulking of a solid tumor, or subjects whose cancers relapsed, or subjects whose cancers are non-metastatic or metastatic.

EXAMPLES

The following examples are not intended to be limiting. Those of skill in the art will, in light of the present disclosure, appreciate that many changes can be made in the specific materials and which are disclosed and still obtain a like or similar result without departing from the spirit and scope of the invention.

Example 1. Determination of Fraction of Quiescent Cancer Cells within a Population The following cell lines were obtained from ATCC and cultured according to the ATCC recommendations: DMS273—small cell lung cancer cell line; H1975—non-small cell lung cancer cell line harboring L858R and T790M mutations in EGFR TK; A549—a non-small cell lung cancer cell line with wild type EGFR; LNCap—prostate cancer cell line; SW620—colon cancer cell line; MiaPaCa2—pancreatic cancer cell line; PANC1—pancreatic cancer cell line; OVCAR3—ovarian cancer cell line; SK-OV-3—ovarian cancer cell line.

Cell cultures were seeded into 6-well plates at $3 \times 10^5$-$6 \times 10^5$ cells/well; the plated number of cells depended on cell size and rate of proliferation, aiming for approximately 50% confluency. After seeding, the cells were allowed to attach for 24 hours while incubated at 37° C. in a humidified 5% $CO_2$ atmosphere, and then treated with compounds for desired amount of time (usually 24 hours) incubating under same conditions. Then the cells were harvested by trypsinization, pooled with the floating cells, washed in PBS, and fixed in 70% ice-cold ethanol overnight. For Acridine Orange (AO) staining, fixed cells were washed once with ice-cold PBS, re-suspended in 100 μL PBS, followed by addition of 200 μL of permeabilizing solution and 600 μL AO staining solution. The measurements were performed with Guava easyCyte HT flow cytometer (EMD Millipore) using the blue laser for excitation at 488 nm, monitoring emission of the AO-DNA complex at 526 nm and AO-RNA complex at 650 nm. The complete protocol and composition of buffers are described in the literature (Darzynkiewicz Z, Juan G, and Srour E F (2004) Differential Staining of DNA and RNA (2004). *Current Protocols in Cytometry*, Chapter 7:Unit 7.3).

Example 2. General Procedure for the Cell Viability Assays

For viability analysis, cells were seeded into 96-well plates at $2 \times 10^3$-$6 \times 10^3$ cells/well; the plated number of cells depended on cell size and rate of proliferation aiming for approximately 50% confluency. After seeding, the cells were allowed to attach for 24 hours incubated at 37° C. in a humidified 5% $CO_2$ atmosphere.

The treatments were performed using at least 6 different concentrations of a compound in 1:3 serial dilutions in DMSO such that the DMSO concentration in the cell medium was <1%. The cell cultures were incubated for an additional 96 hours in 5% $CO_2$ incubator at 37° C. Treatments were performed in triplicate. Results were analyzed by CellTiter-Glo™ Luminescent Cell Viability Assay (Promega, cat. #G7571) according to the manufacturer's instructions using Spectra MAX Gemini Spectrophotometer (Molecular Devices).

Figure 1:
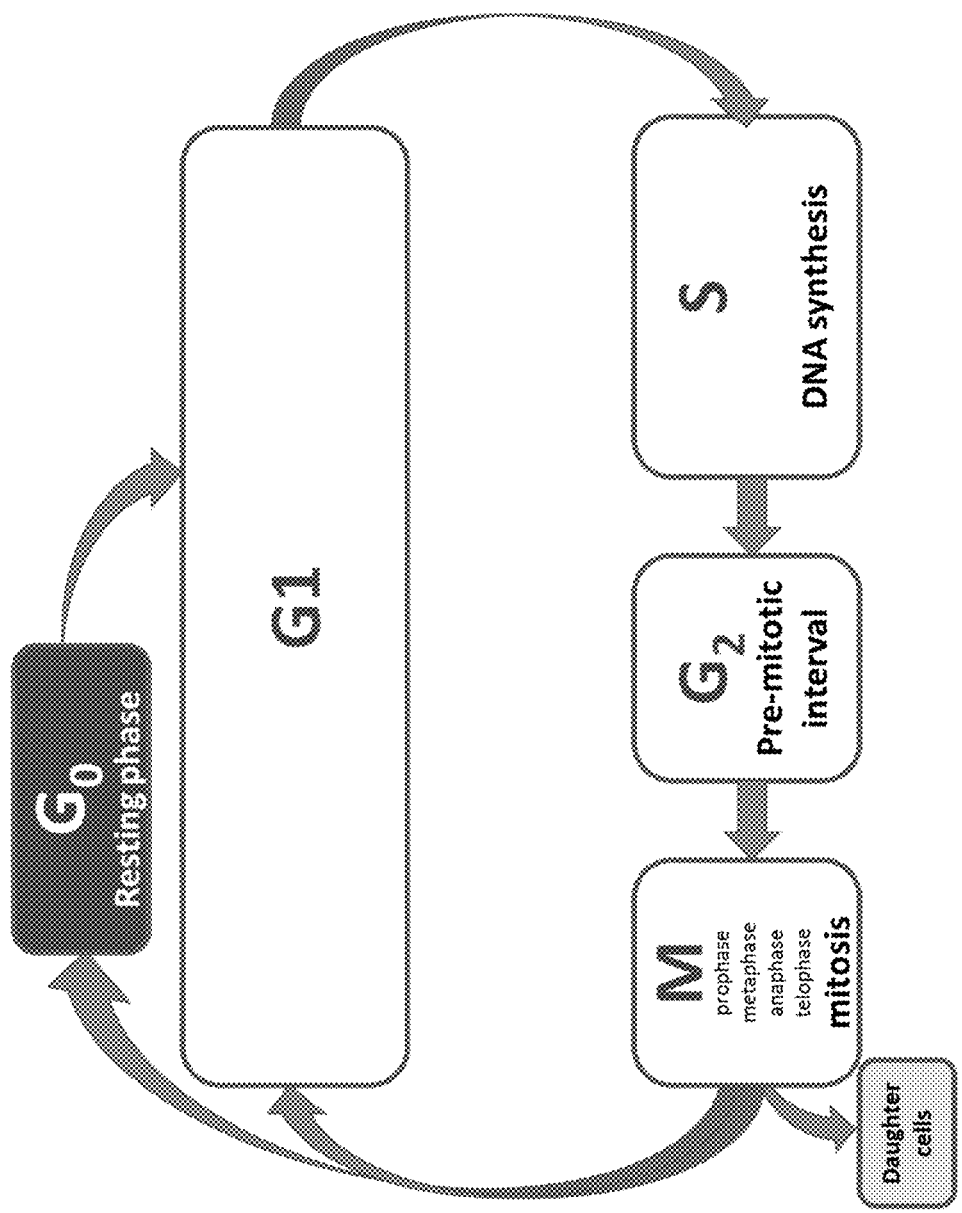
FIG. 1 shows a schematic diagram of a mitotic cycle of a eukaryotic cell.
Figure 2:
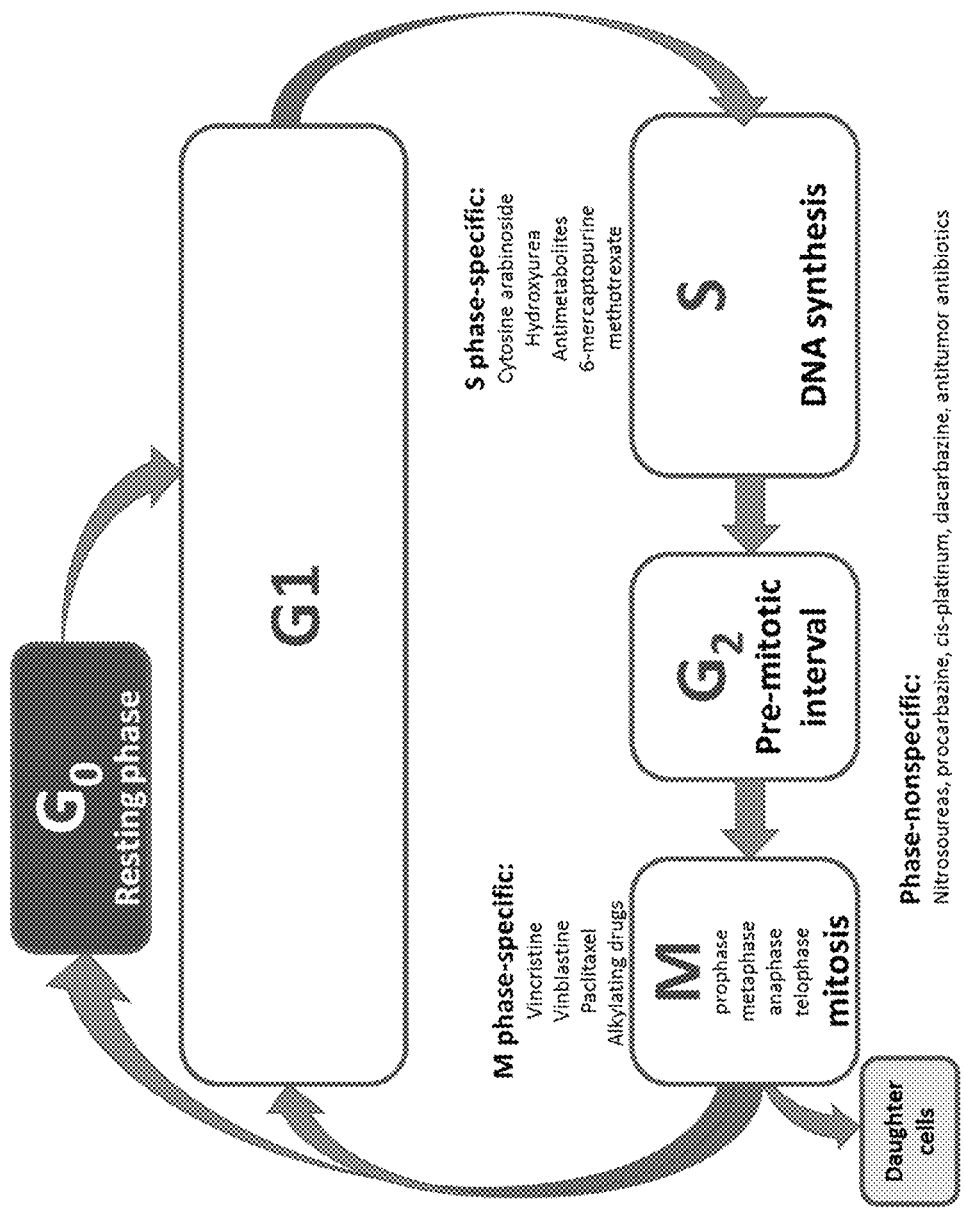
FIG. 2 shows a schematic diagram of a mitotic cycle of a eukaryotic cancer cell annotated to indicate the stages of the cell cycle upon which some of the available anti-cancer therapeutic agents are believed act.
Figure 3:
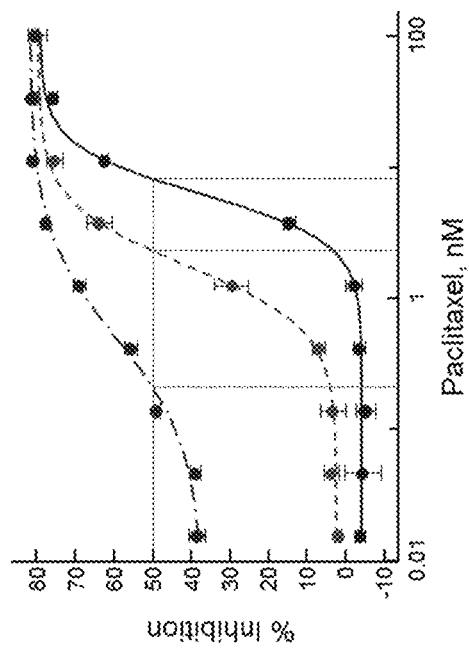
FIG. 3 shows effect of combination of paclitaxel and Compound I-5 (0, 2, and 4 µM) on the growth of SW620 cells.

Example 3. Combination of a Molecule Effective Against Quiescent Cancer Cells with Paclitaxel SW620 cells were cultured, treated, and analyzed as described in Examples 1 and 2. The highest concentration of paclitaxel used in this assay was 100 nM and the concentrations of Compound I-5 were 2 μM and 4 μM, accordingly. The observed $EC_{50}$ values of paclitaxel were 8.1 nM when Compound I-5 was not present, 2.3 nM when Compound I-5 was present at a concentration of 2 μM, and 0.2 nM when Compound I-5 was present at a concentration of 4 μM. See FIG. 3.

Figure 4:
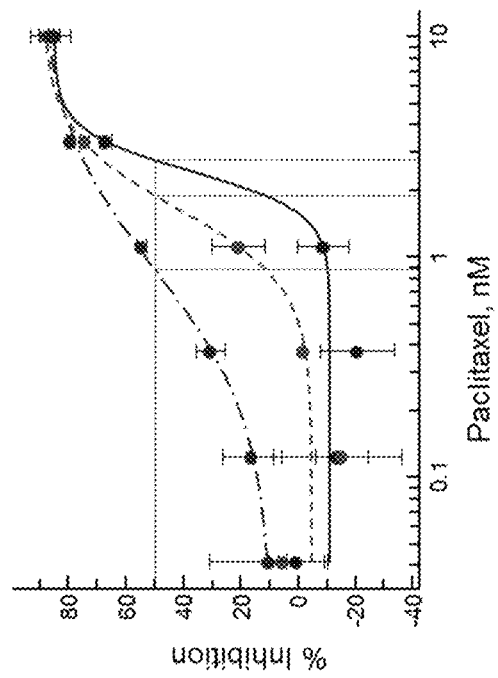
FIG. 4 shows effect of combination of paclitaxel and Compound I-7 (0, 2, and 4 µM) on the growth of DMS273 cells.

DMS273 cells were cultured, treated, and analyzed as described in Examples 1 and 2. The highest concentration of paclitaxel used in this assay was 10 nM and the concentrations of Compound I-7 were 2 μM and 4 μM. The observed $EC_{50}$ values of paclitaxel were 2.7 nM when Compound I-7 was not present, 1.9 nM when Compound I-7 was present at a concentration of 2 μM, and 0.9 nM when Compound I-7 was present at a concentration of 4 μM. See FIG. 4.

Figure 5:
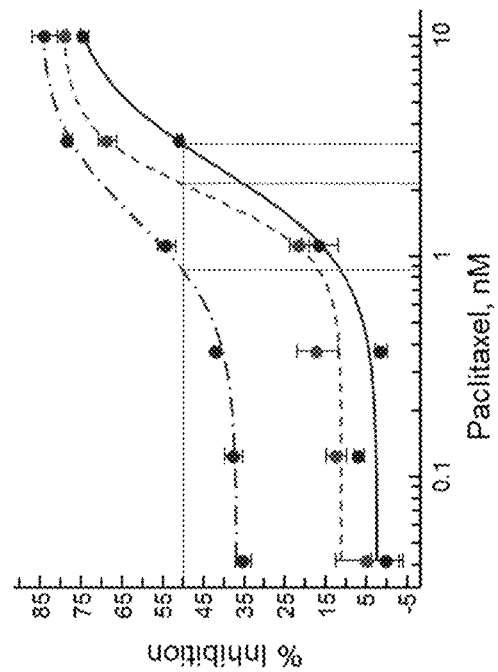
FIG. 5 shows effect of combination of paclitaxel and Compound I-5 (0, 2, and 4 µM) on the growth of LNCap cells.

LNCap cells were cultured, treated, and analyzed as described in Examples 1 and 2. The highest concentration of paclitaxel used in this assay was 10 nM and the concentrations of Compound I-5 were 2 μM and 4 μM. The observed $EC_{50}$ values of paclitaxel were 3.2 nM when Compound I-5 was not present, 2.1 nM when Compound I-5 was present at a concentration of 2 μM, and 0.9 nM when Compound I-5 was present at a concentration of 4 μM. See FIG. 5.

Figure 6:
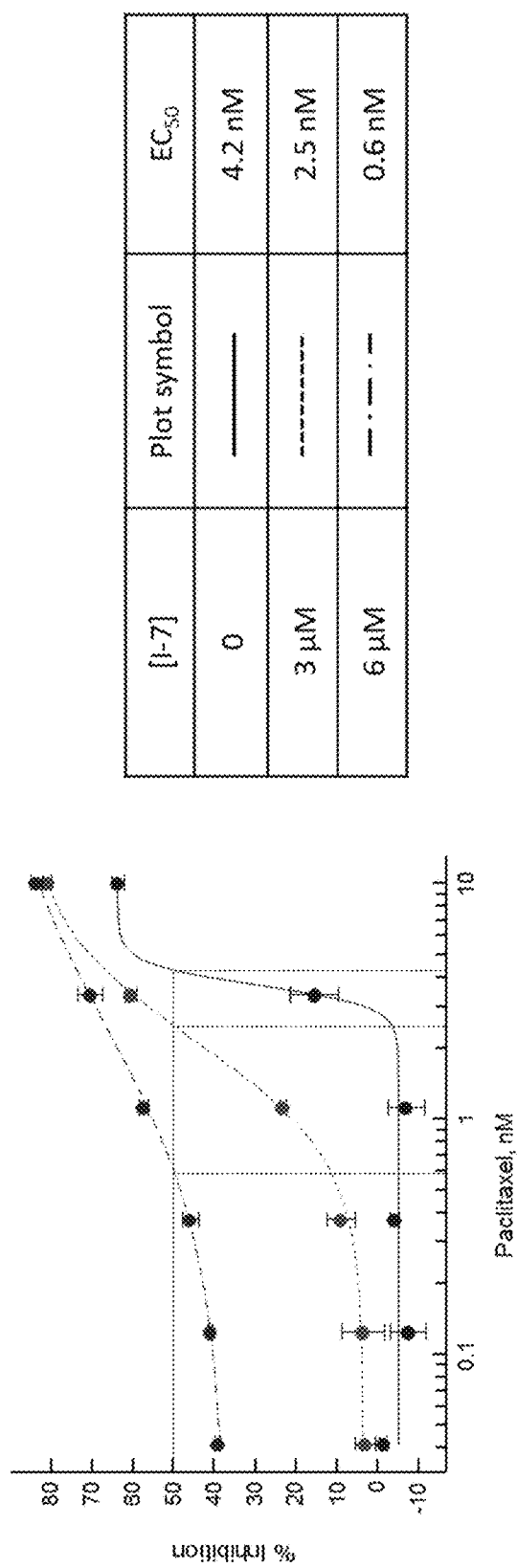
FIG. 6 shows effect of combination of paclitaxel and Compound I-7 (0, 3, and 6 µM) on the growth of HCC827 cells.

HCC827 cells were cultured, treated, and analyzed as described in Examples 1 and 2. The highest concentration of paclitaxel used in this assay was 10 nM and the concentrations of Compound I-7 were 3 μM and 6 μM. The observed $EC_{50}$ values of paclitaxel were 4.2 nM when Compound I-7 was not present, 2.5 nM when Compound I-7 was present at a concentration of 3 μM, and 0.6 nM when Compound I-7 was present at a concentration of 6 μM. See FIG. 6.

Figure 7:
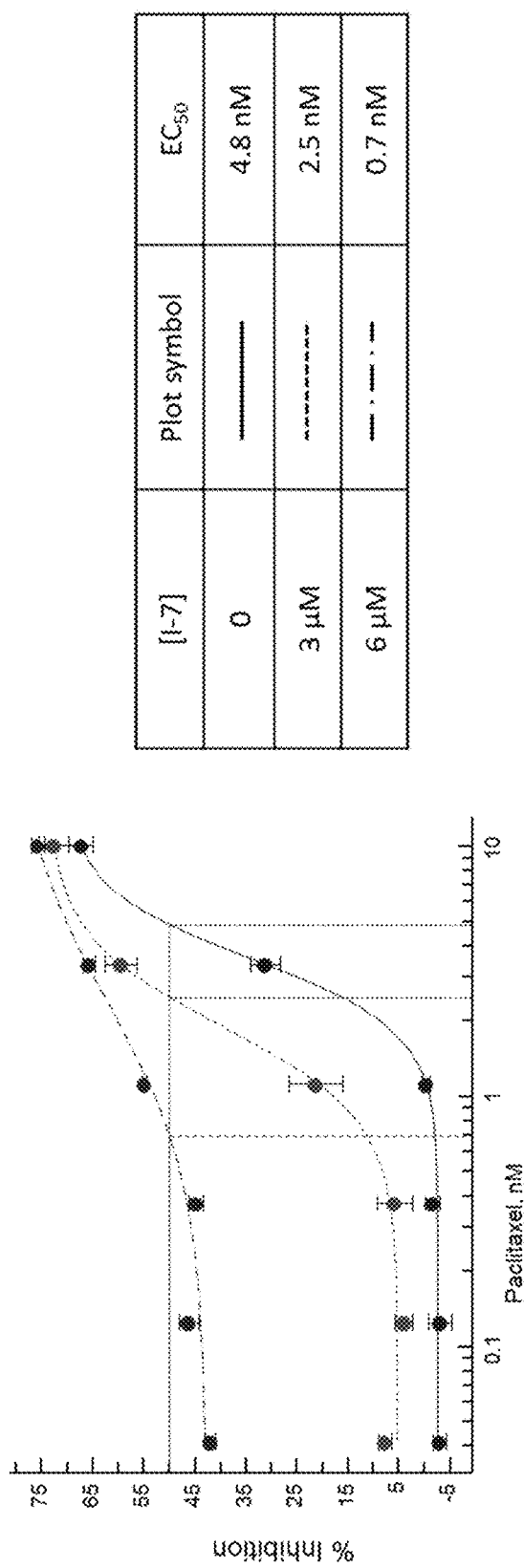
FIG. 7 shows effect of combination of paclitaxel and Compound I-7 (0, 3, and 6 µM) on the growth of A549 cells.

A549 cells were cultured, treated, and analyzed as described in Examples 1 and 2. The highest concentration of paclitaxel used in this assay was 10 nM and the concentrations of Compound I-7 were 3 μM and 6 μM. The observed $EC_{50}$ values of paclitaxel were 4.8 nM when Compound I-7 was not present, 2.5 nM when Compound I-7 was present at a concentration of 3 μM, and 0.7 nM when Compound I-7 was present at a concentration of 6 μM. See FIG. 7.

Figure 8:
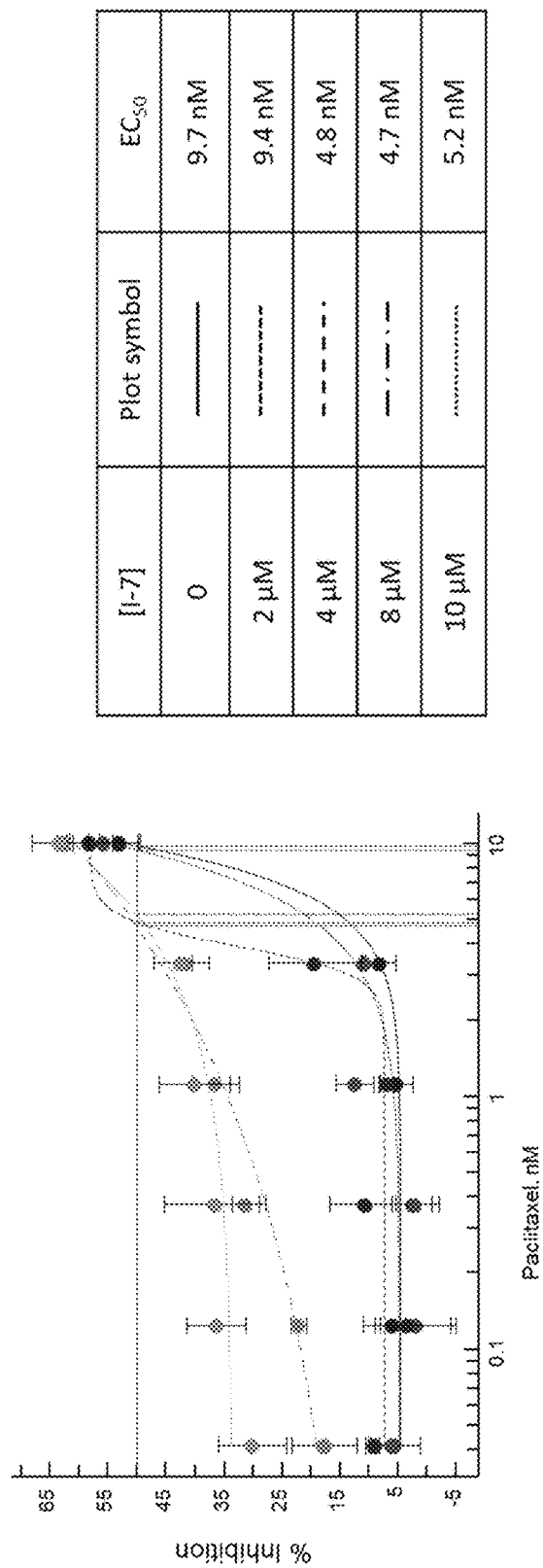
FIG. 8 shows effect of combination of paclitaxel and Compound I-7 (0, 2, 4, 8, and 10 µM) on the growth of SK-OV-3 cells.

SK-OV-3 cells were cultured, treated, and analyzed as described in Examples 1 and 2. The highest concentration of paclitaxel used in this assay was 10 nM and the concentrations of Compound I-7 were 2 μM, 4 μM, 8 μM, and 10 μM. The observed $EC_{50}$ values of paclitaxel were 9.7 nM when Compound I-7 was not present, 9.4 nM when Compound I-7 was present at a concentration of 2 μM, 4.8 nM when Compound I-7 was present at a concentration of 4 μM, 4.7 nM when Compound I-7 was present at a concentration of 8 μM, and 5.2 nM when Compound I-7 was present at a concentration of 10 μM. See FIG. 8.

Figure 9:
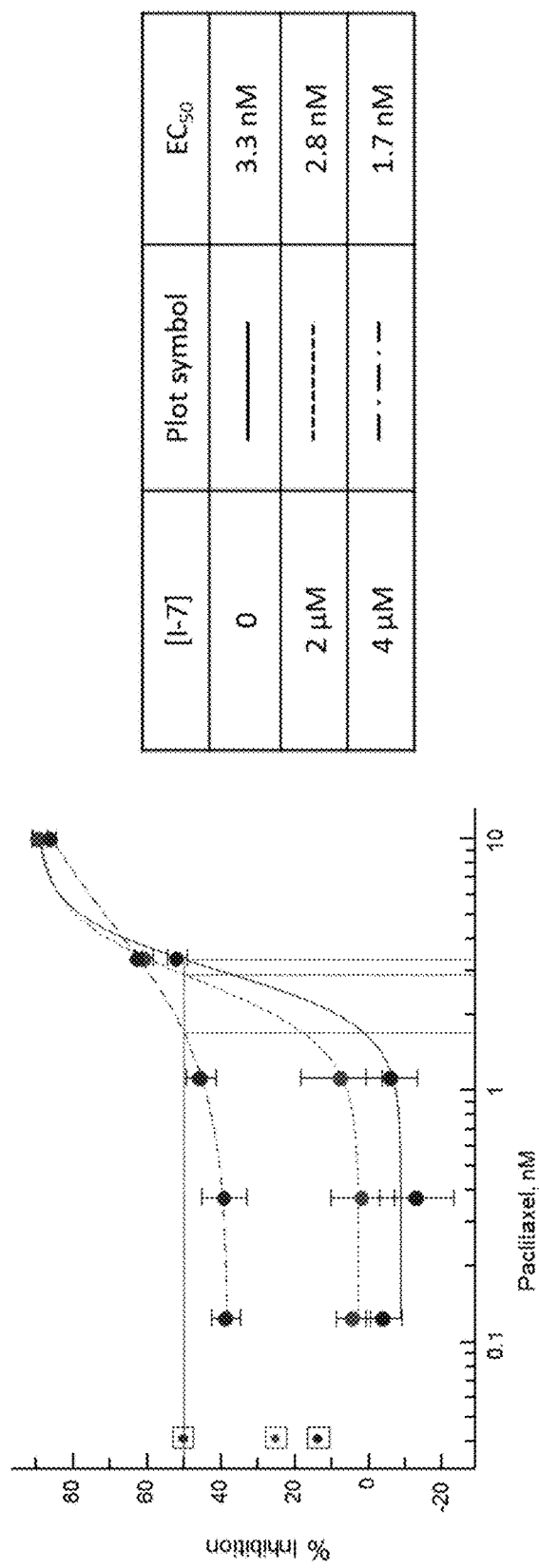
FIG. 9 shows effect of combination of paclitaxel and Compound I-7 (0, 2, and 4 µM) on the growth of OVCAR3 cells.

OVCAR3 cells were cultured, treated, and analyzed as described in Examples 1 and 2. The highest concentration of paclitaxel used in this assay was 10 nM and the concentrations of Compound I-7 were 2 μM and 4 μM. The observed $EC_{50}$ values of paclitaxel were 3.3 nM when Compound I-7 was not present, 2.8 nM when Compound I-7 was present at a concentration of 3 μM, and 1.7 nM when Compound I-7 was present at a concentration of 6 μM. See FIG. 9.

Figure 10:
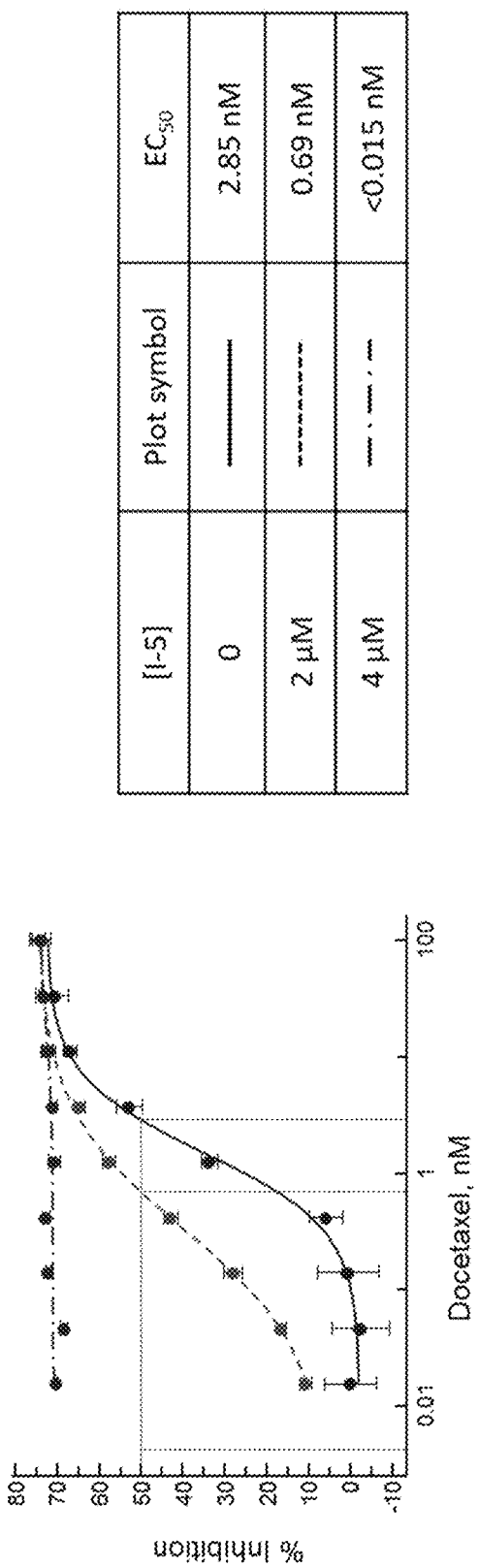
FIG. 10 shows effect of combination of docetaxel and Compound I-5 (0, 2, and 4 µM) on the growth of SW620 cells.

Example 4. Combination of a Molecule Effective Against Quiescent Cancer Cells with Docetaxel SW620 cells were cultured, treated, and analyzed as described in Examples 1 and 2. The highest concentration of docetaxel used in this assay was 100 nM and the concentrations of Compound I-5 were 2 μM and 4 μM. The observed $EC_{50}$ values of docetaxel were 2.85 nM when Compound I-5 was not present, 0.69 nM when Compound I-5 was present at a concentration of 2 μM, and <0.015 nM when Compound I-5 was present at a concentration of 4 μM. See FIG. 10.

Figure 11:
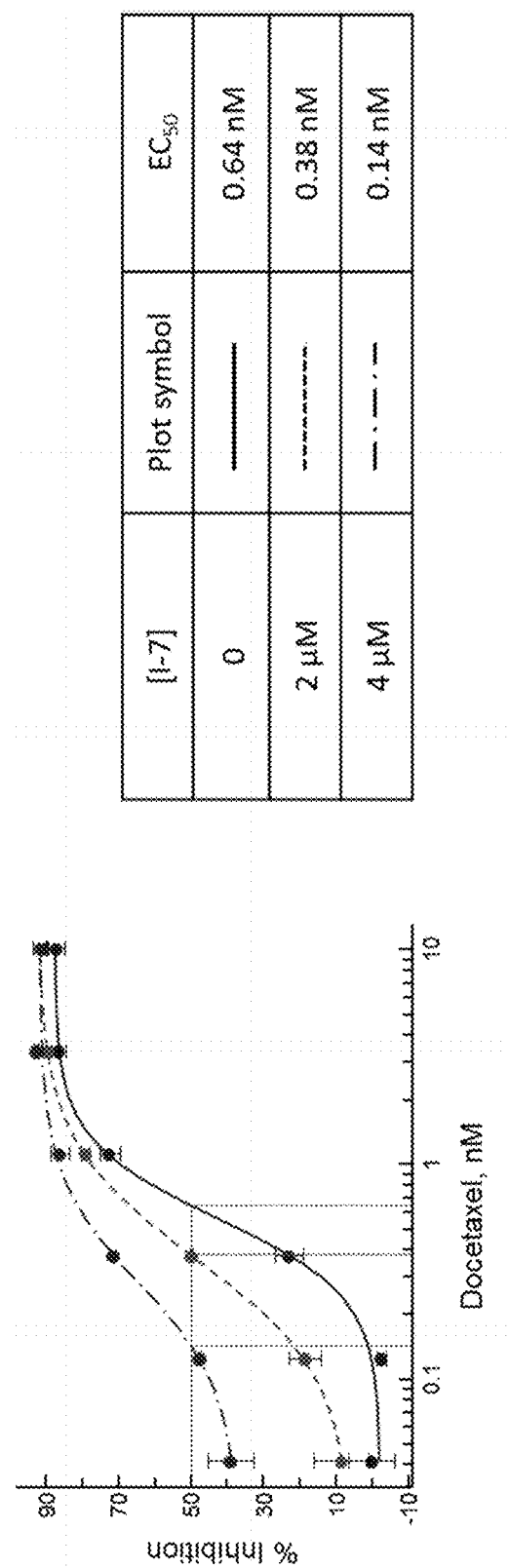
FIG. 11 shows effect of combination of docetaxel and Compound I-7 (0, 2, and 4 µM) on the growth of DMS273 cells.

DMS273 cells were cultured, treated, and analyzed as described in Examples 1 and 2. The highest concentration of docetaxel used in this assay was 10 nM and the concentrations of Compound I-7 were 2 μM and 4 μM. The observed $EC_{50}$ values of docetaxel were 0.64 nM when Compound I-7 was not present, 0.38 nM when Compound I-7 was present at a concentration of 2 μM, and 0.14 nM when Compound I-7 was present at a concentration of 4 μM. See FIG. 11.

Figure 12:
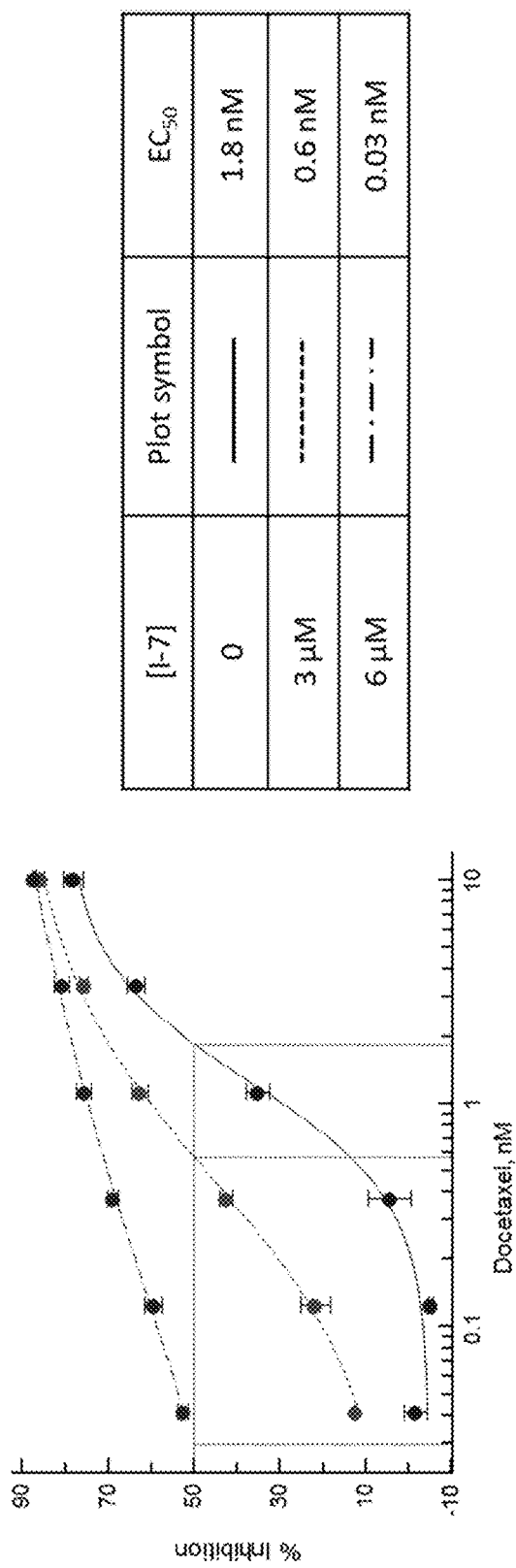
FIG. 12 shows effect of combination of docetaxel and Compound I-7 (0, 3, and 6 µM) on the growth of HCC827 cells.

HCC827 cells were cultured, treated, and analyzed as described in Examples 1 and 2. The highest concentration of docetaxel used in this assay was 10 nM and the concentrations of Compound I-7 were 3 μM and 6 μM. The observed $EC_{50}$ values of docetaxel were 1.8 nM when Compound I-7 was not present, 0.6 nM when Compound I-7 was present at a concentration of 2 μM, and 0.03 nM when Compound I-7 was present at a concentration of 4 μM. See FIG. 12.

Figure 13:
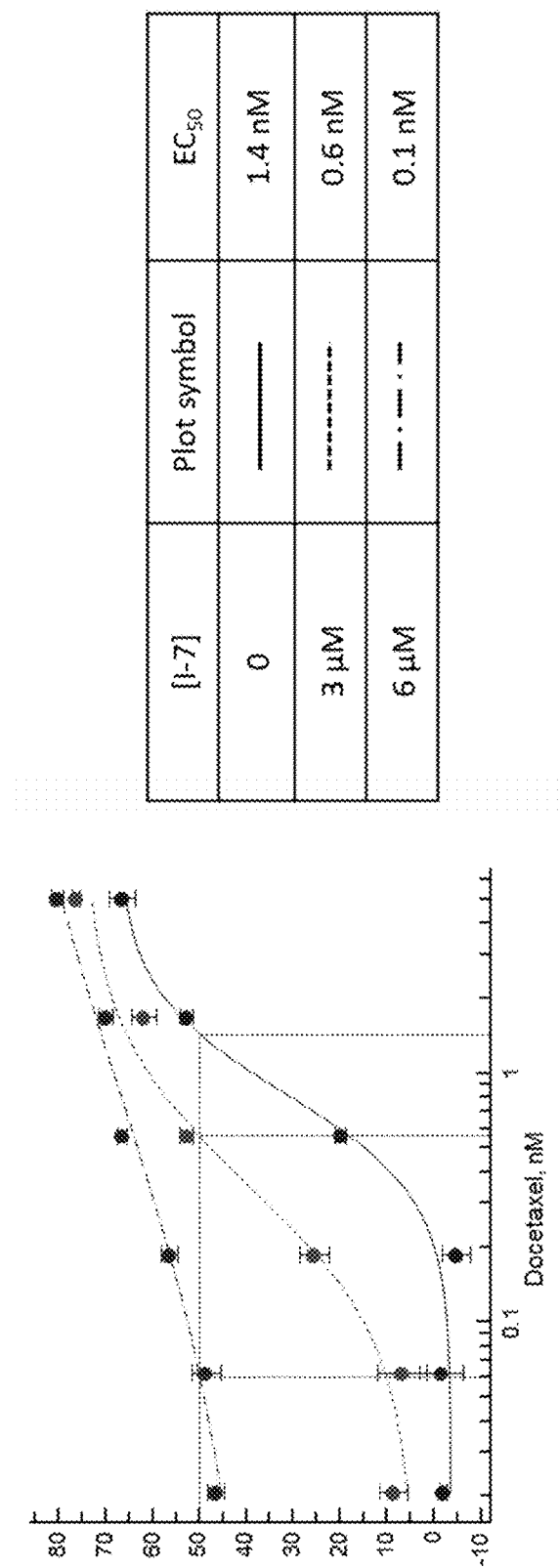
FIG. 13 shows effect of combination of docetaxel and Compound I-7 (0, 3, and 6 µM) on the growth of A549 cells.

A549 cells were cultured, treated, and analyzed as described in Examples 1 and 2. The highest concentration of docetaxel used in this assay was 5 nM and the concentrations of Compound I-7 were 3 μM and 6 μM. The observed $EC_{50}$ values of docetaxel were 1.4 nM when Compound I-7 was not present, 0.6 nM when Compound I-7 was present at a concentration of 2 μM, and 0.1 nM when Compound I-7 was present at a concentration of 4 μM. See FIG. 13.

Figure 14:
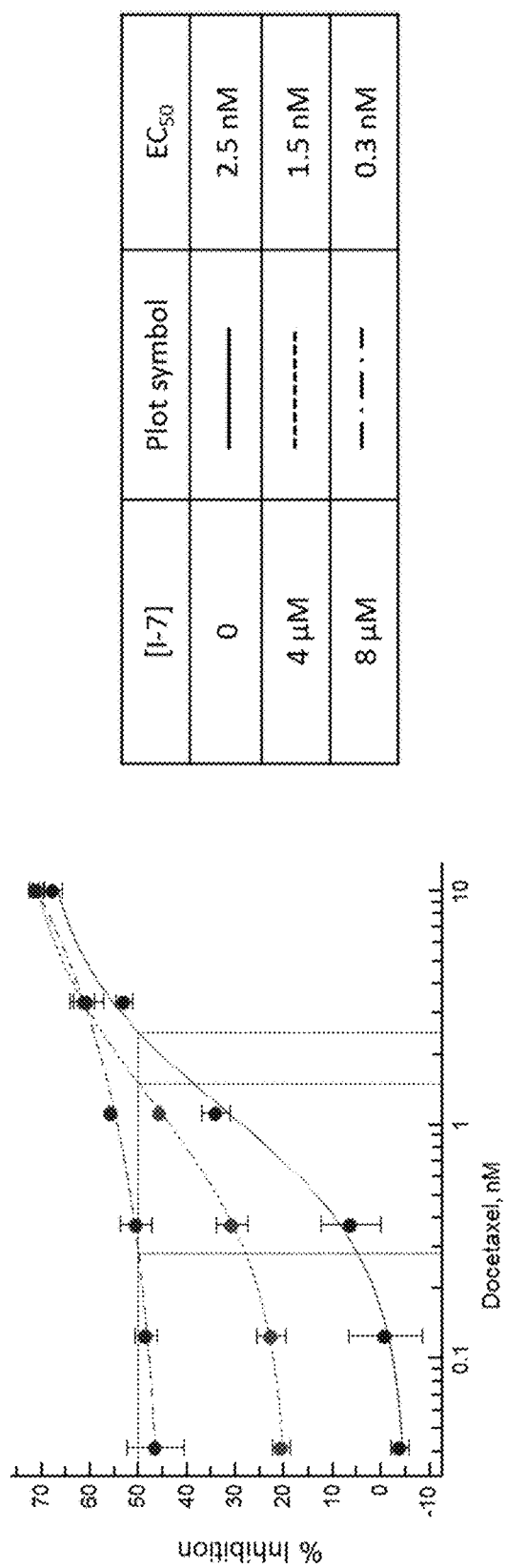
FIG. 14 shows effect of combination of docetaxel and Compound I-7 (0, 4, and 8 µM) on the growth of SK-OV-3 cells.

SK-OV-3 cells were cultured, treated, and analyzed as described in Examples 1 and 2. The highest concentration of docetaxel used in this assay was 10 nM and the concentrations of Compound I-7 were 4 μM and 8 μM. The observed $EC_{50}$ values of docetaxel were 2.5 nM when Compound I-7 was not present, 1.5 nM when Compound I-7 was present at a concentration of 2 μM, and 0.3 nM when Compound I-7 was present at a concentration of 4 μM. See FIG. 14.

Figure 15:
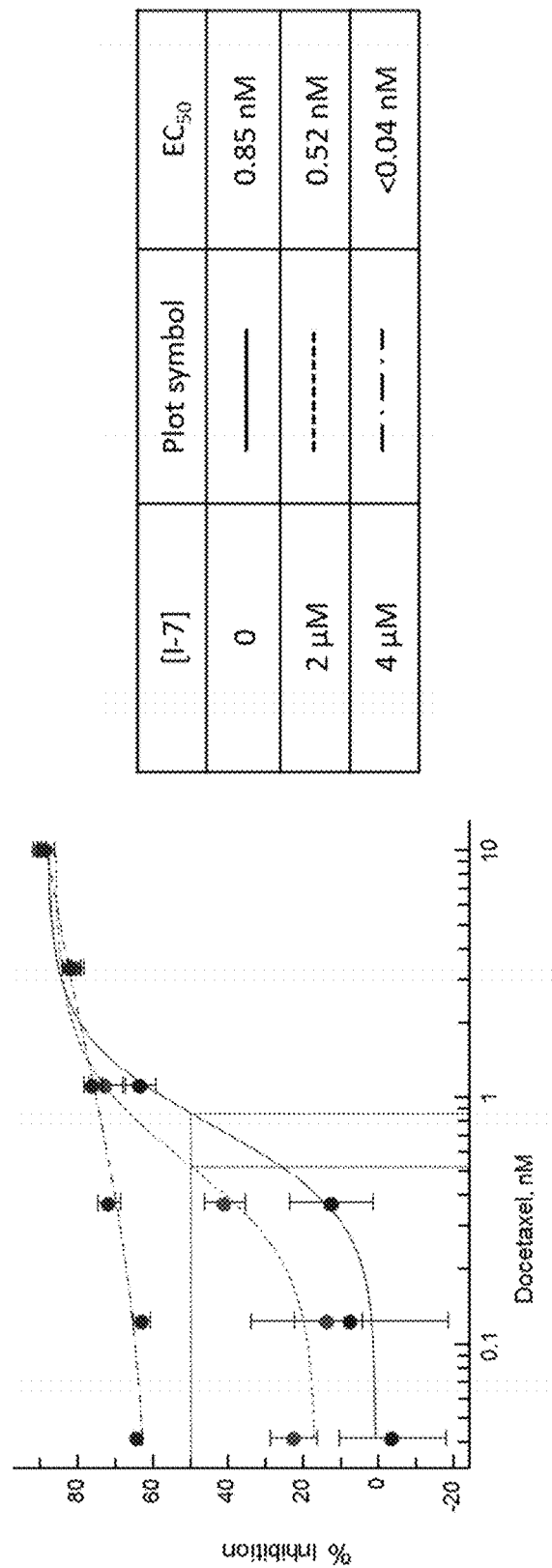
FIG. 15 shows effect of combination of docetaxel and Compound I-7 (0, 2, and 4 µM) on the growth of OVCAR3 cells.

OVCAR3 cells were cultured, treated, and analyzed as described in Examples 1 and 2. The highest concentration of docetaxel used in this assay was 10 nM and the concentrations of Compound I-7 were 2 μM and 4 μM. The observed $EC_{50}$ values of docetaxel were 0.85 nM when Compound I-7 was not present, 0.52 nM when Compound I-7 was present at a concentration of 2 μM, and <0.04 nM when Compound I-7 was present at a concentration of 4 μM. See FIG. 15.

Figure 16:
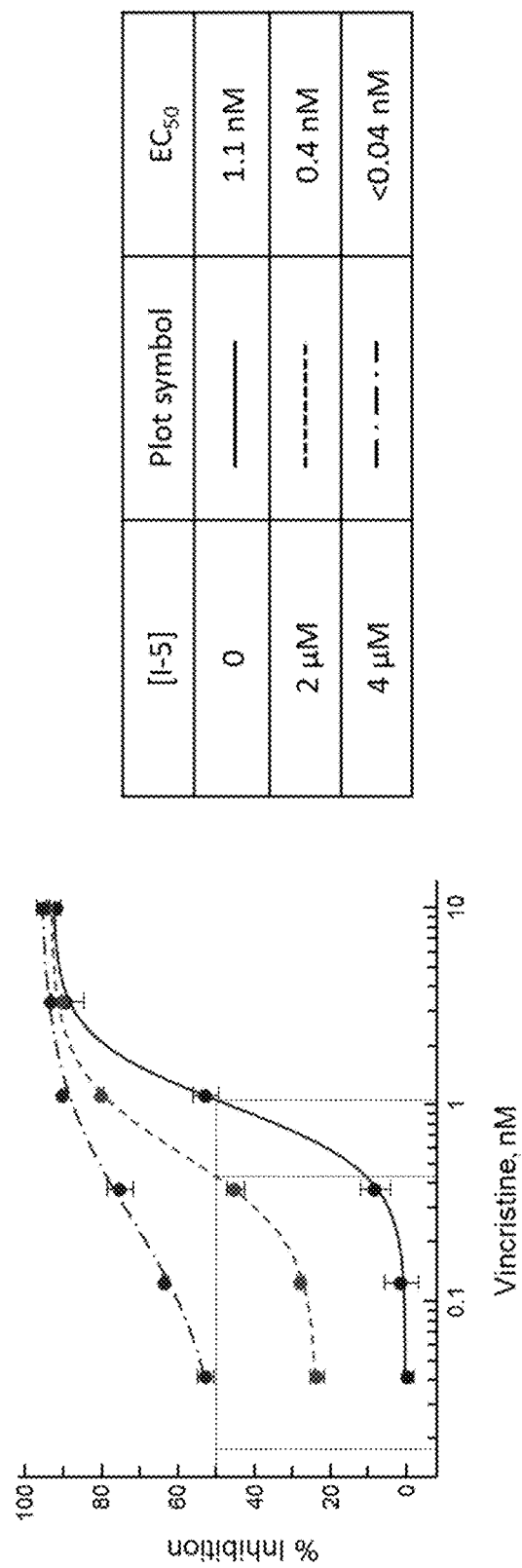
FIG. 16 effect of combination of vincristine and Compound I-5 (0, 2, and 4 µM) on the growth of DMS273 cells.

Example 5. Combination of a Molecule Effective Against Quiescent Cancer Cells with Vincristine DMS273 cells were cultured, treated, and analyzed as described in Examples 1 and 2. The highest concentration of vincristine used in this assay was 10 nM and the concentrations of Compound I-5 were 2 μM and 4 μM. The observed $EC_{50}$ values of vincristine were 1.1 nM when Compound I-5 was not present, 0.4 nM when Compound I-5 was present at a concentration of 2 μM, and <0.04 nM when Compound I-5 was present at a concentration of 4 μM. See FIG. 16.

Figure 17:
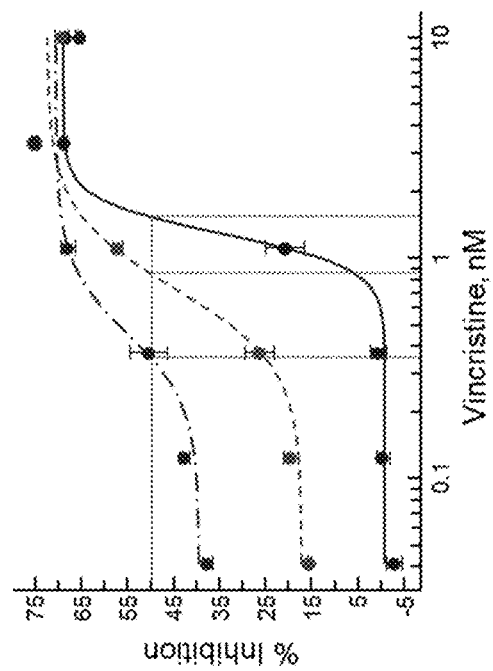
FIG. 17 shows effect of combination of vincristine and Compound I-5 (0, 2, and 4 µM) on the growth of H1975 cells.

H1975 cells were cultured, treated, and analyzed as described in Examples 1 and 2. The highest concentration of vincristine used in this assay was 10 nM and the concentrations of Compound I-5 were 2 μM and 4 μM. The observed $EC_{50}$ values of vincristine were 1.5 nM when Compound I-5 was not present, 0.85 nM when Compound I-5 was present at a concentration of 2 μM, and 0.35 nM when Compound I-5 was present at a concentration of 4 μM. See FIG. 17.

Figure 18:
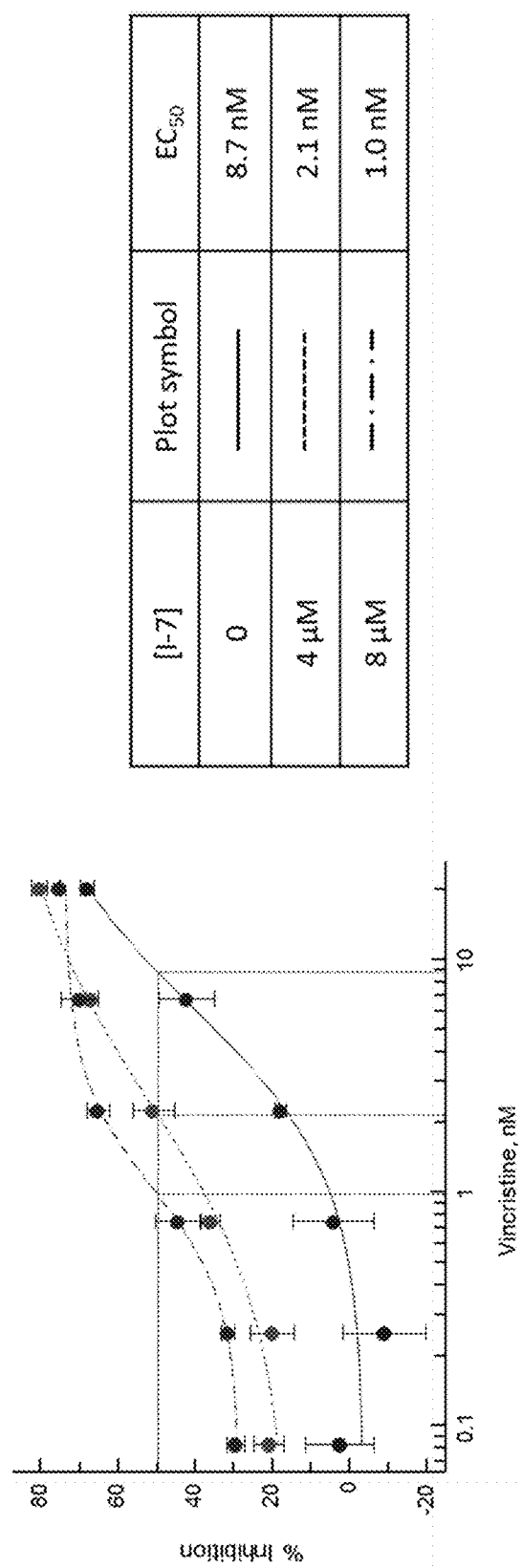
FIG. 18 shows effect of combination of vincristine and Compound I-7 (0, 4, and 8 µM) on the growth of SK-OV-3 cells.

SK-OV-3 cells were cultured, treated, and analyzed as described in Examples 1 and 2. The highest concentration of vincristine used in this assay was 20 nM and the concentrations of Compound I-7 were 4 μM and 8 μM. The observed $EC_{50}$ values of vincristine were 8.7 nM when Compound I-7 was not present, 2.1 nM when Compound I-7 was present at a concentration of 4 μM, and 1.0 nM when Compound I-7 was present at a concentration of 8 μM. See FIG. 18.

Figure 19:
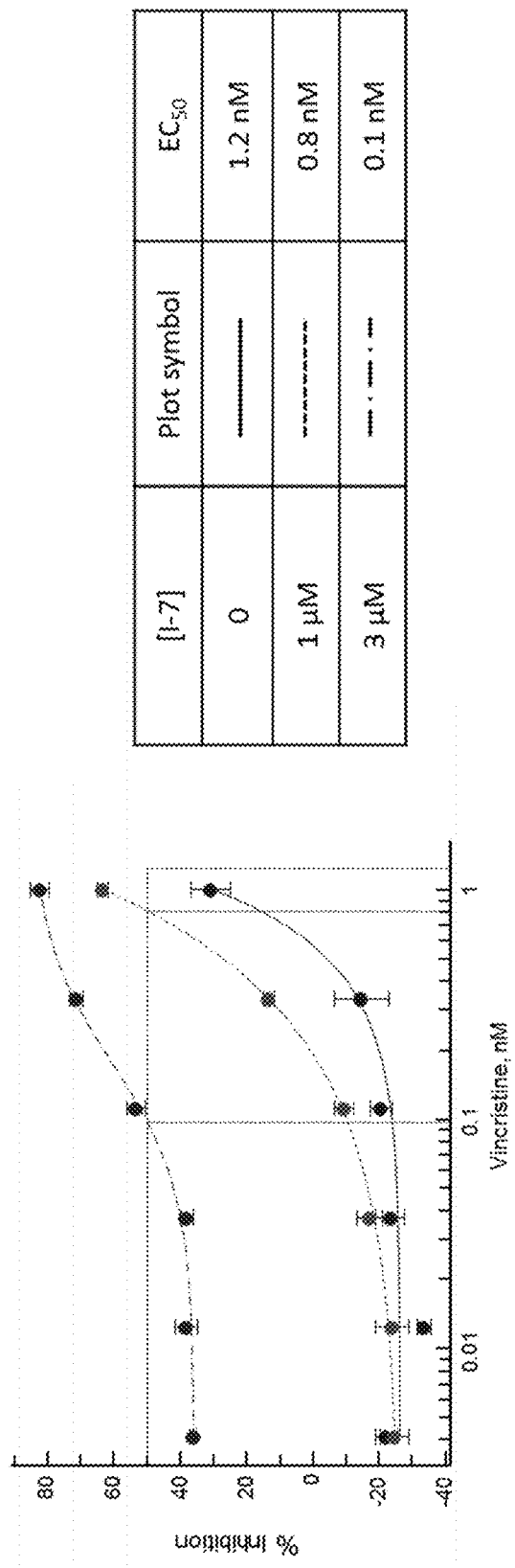
FIG. 19 shows effect of combination of vincristine and Compound I-7 (0, 1, and 3 µM) on the growth of OVCAR3 cells.

OVCAR3 cells were cultured, treated, and analyzed as described in Examples 1 and 2. The highest concentration of vincristine used in this assay was 1 nM and the concentrations of Compound I-7 were 1 μM and 3 μM. The observed $EC_{50}$ values of vincristine were 1.2 nM when Compound I-7 was not present, 0.8 nM when Compound I-7 was present at a concentration of 2 μM, and 0.1 nM when Compound I-7 was present at a concentration of 4 μM. See FIG. 19.

Figure 20:
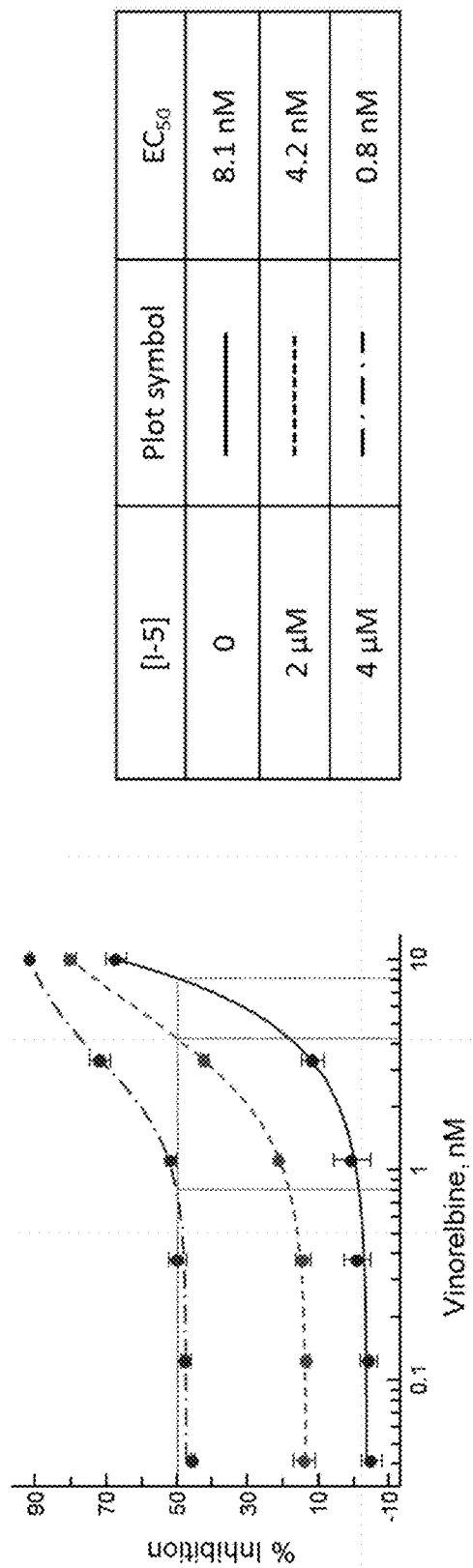
FIG. 20 shows effect of combination of vinorelbine and Compound I-5 (0, 2, and 4 µM) on the growth of DMS273 cells.

Example 6. Combination of a Molecule Effective Against Quiescent Cancer Cells with Vinorelbine DMS273 cells were cultured, treated, and analyzed as described in Examples 1 and 2. The highest concentration of vinorelbine used in this assay was 10 nM and the concentrations of Compound I-5 were 2 μM and 4 μM. The observed $EC_{50}$ values of vinorelbine were 1.1 nM when Compound I-5 was not present, 0.4 nM when Compound I-5 was present at a concentration of 2 μM, and <0.04 nM when Compound I-5 was present at a concentration of 4 μM. See FIG. 20.

Figure 21:
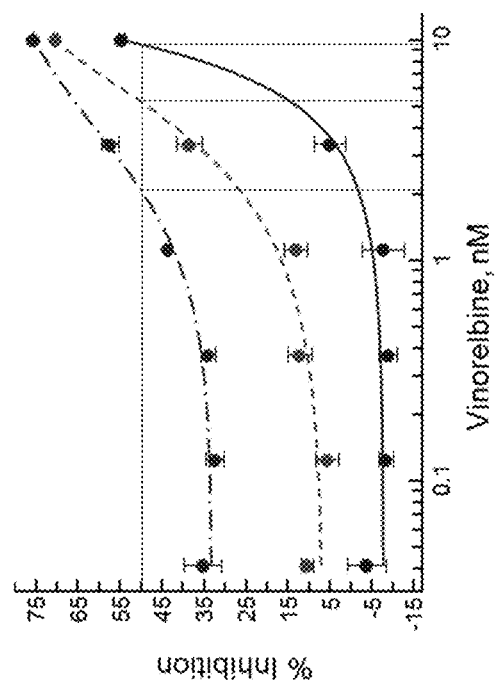
FIG. 21 shows effect of combination of vinorelbine and Compound I-5 (0, 2, and 4 µM) on the growth of H1975 cells.

H1975 cells were cultured, treated, and analyzed as described in Examples 1 and 2. The highest concentration of vinorelbine used in this assay was 10 nM and the concentrations of Compound I-5 were 2 μM and 4 μM. The observed $EC_{50}$ values of vinorelbine were 9.5 nM when Compound I-5 was not present, 5.2 nM when Compound I-5 was present at a concentration of 2 μM, and 2.1 nM when Compound I-5 was present at a concentration of 4 μM. See FIG. 21.

Figure 22:
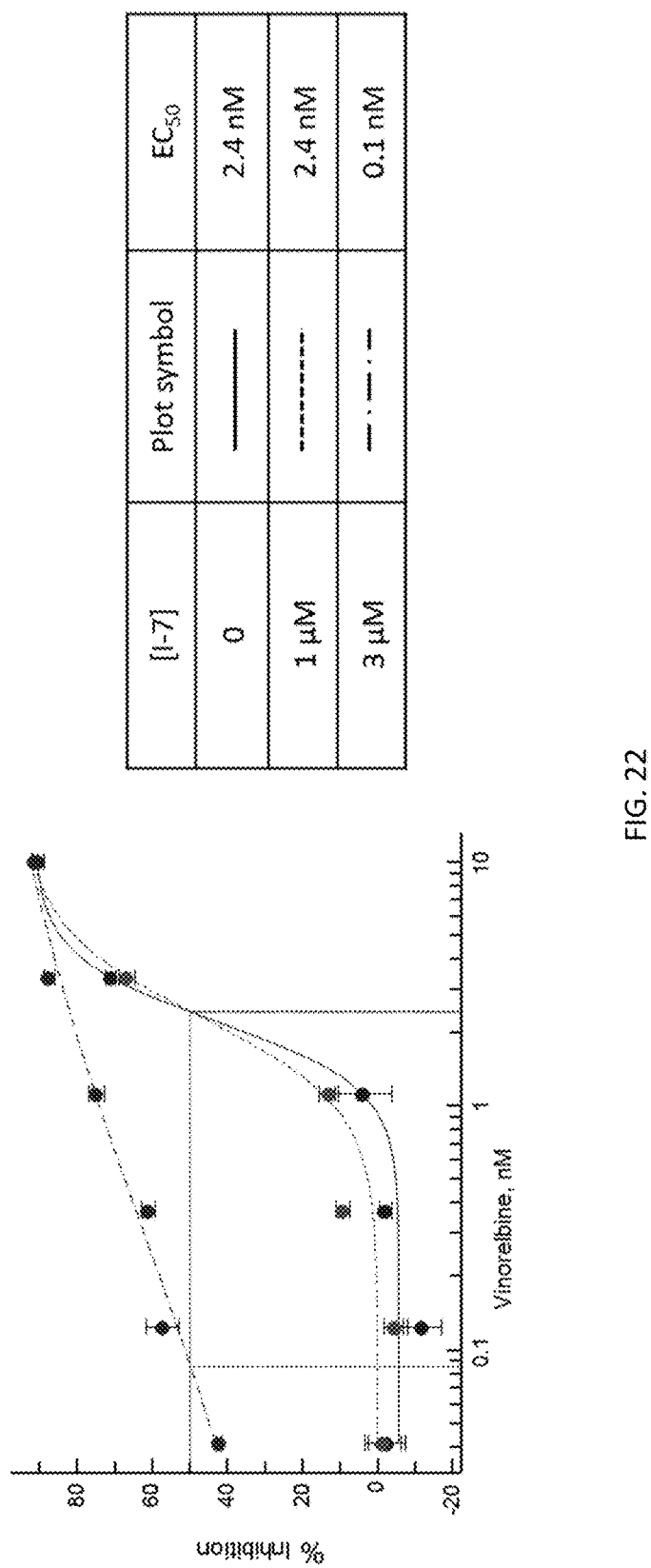
FIG. 22 shows effect of combination of vinorelbine and Compound I-7 (0, 1, and 3 µM) on the growth of OVCAR3 cells.

OVCAR3 cells were cultured, treated, and analyzed as described in Examples 1 and 2. The highest concentration of vinorelbine used in this assay was 10 nM and the concentrations of Compound I-7 were 1 μM and 3 μM. The observed $EC_{50}$ values of vinorelbine were 2.4 nM when Compound I-7 was not present, 2.4 nM when Compound I-7 was present at a concentration of 1 μM, and 0.1 nM when Compound I-7 was present at a concentration of 3 μM. See FIG. 22.

Figure 23:
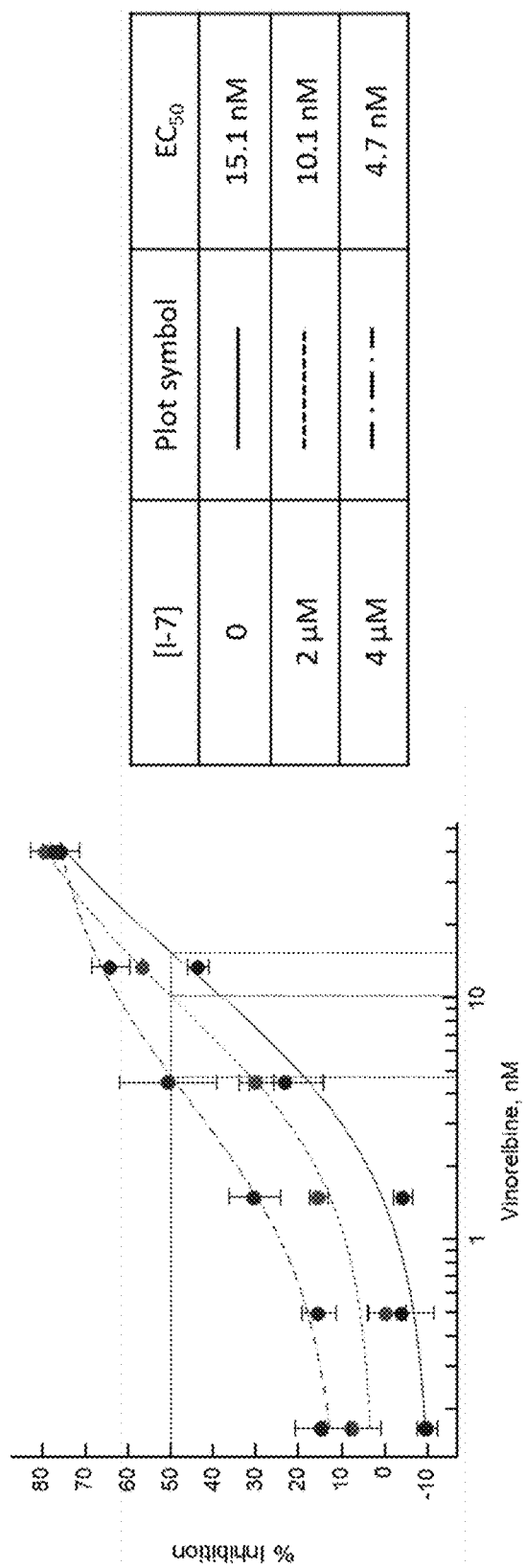
FIG. 23 shows effect of combination of vincristine and Compound I-7 (0, 4, and 8 µM) on the growth of SK-OV-3 cells.

SK-OV-3 cells were cultured, treated, and analyzed as described in Examples 1 and 2. The highest concentration of vinorelbine used in this assay was 40 nM and the concentrations of Compound I-7 were 2 μM and 4 μM. The observed $EC_{50}$ values of vinorelbine were 15.1 nM when Compound I-7 was not present, 10.1 nM when Compound I-7 was present at a concentration of 2 μM, and 4.7 nM when Compound I-7 was present at a concentration of 4 μM. See FIG. 23.

Figure 24:
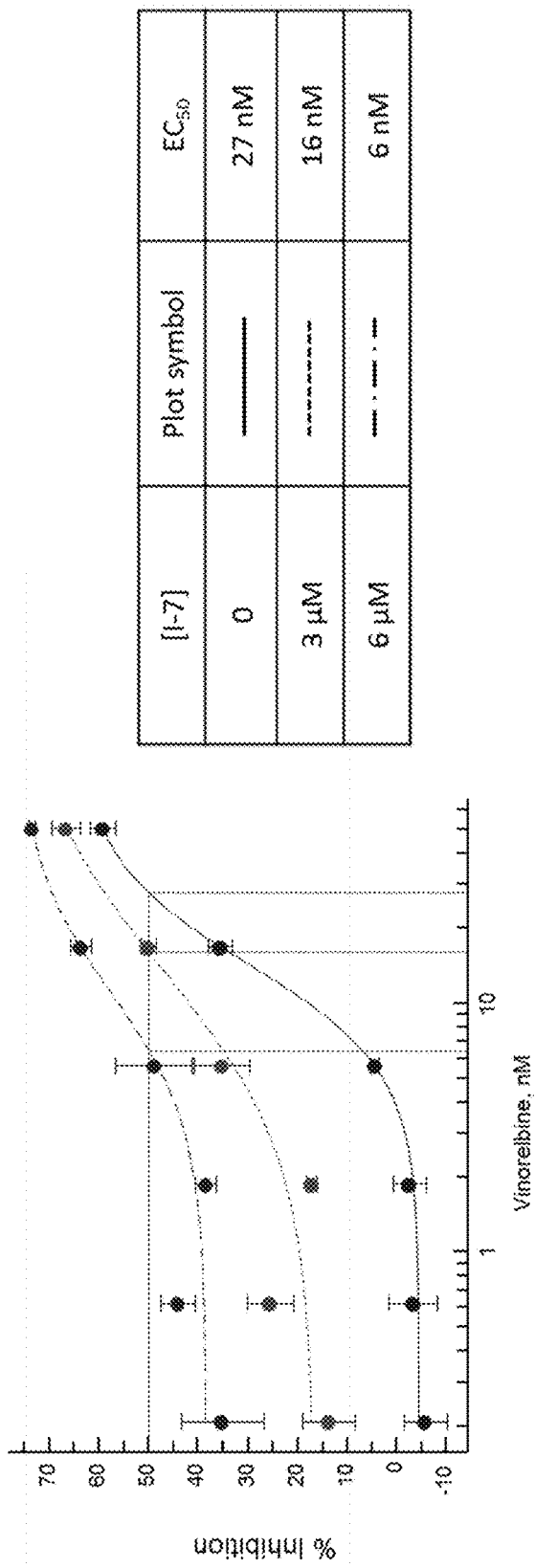
FIG. 24 shows effect of combination of vincristine and Compound I-7 (0, 3, and 6 µM) on the growth of A549 cells.

A549 cells were cultured, treated, and analyzed as described in Examples 1 and 2. The highest concentration of vinorelbine used in this assay was 50 nM and the concentrations of Compound I-7 were 2 μM and 4 μM. The observed $EC_{50}$ values of vinorelbine were 27 nM when Compound I-7 was not present, 16 nM when Compound I-7 was present at a concentration of 2 µM, and 6 nM when Compound I-7 was present at a concentration of 4 µM. See FIG. 24.

Example 7. Combination of a Molecule Effective Against Quiescent Cancer Cells with BI2536

Figure 25:
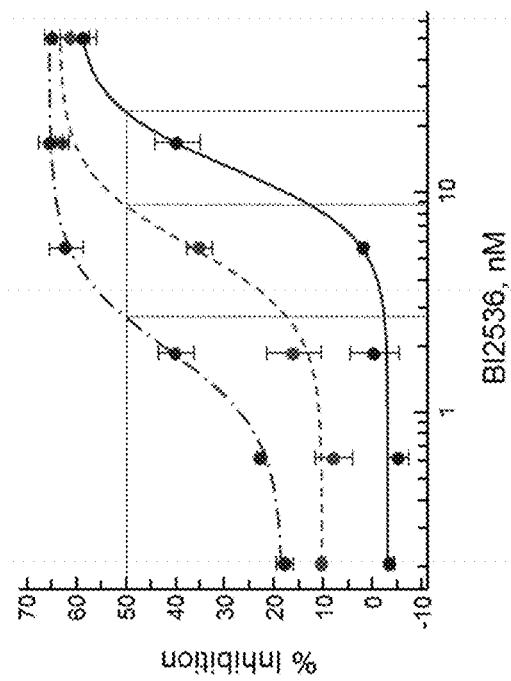
FIG. 25 shows effect of combination of B12536 and Compound I-7 (0, 2, and 4 µM) on the growth of H1975 cells.

H1975 cells were cultured, treated, and analyzed as described in Examples 1 and 2. The highest concentration of BI2536 used in this assay was 50 nM and the concentrations of Compound I-7 were 2 µM and 4 µM. The observed $EC_{50}$ values of BI2536 were 46.3 nM when Compound I-7 was not present, 17.3 nM when Compound I-7 was present at a concentration of 2 µM, and <0.04 nM when Compound I-7 was present at a concentration of 4 µM. See FIG. 25.

Figure 26:
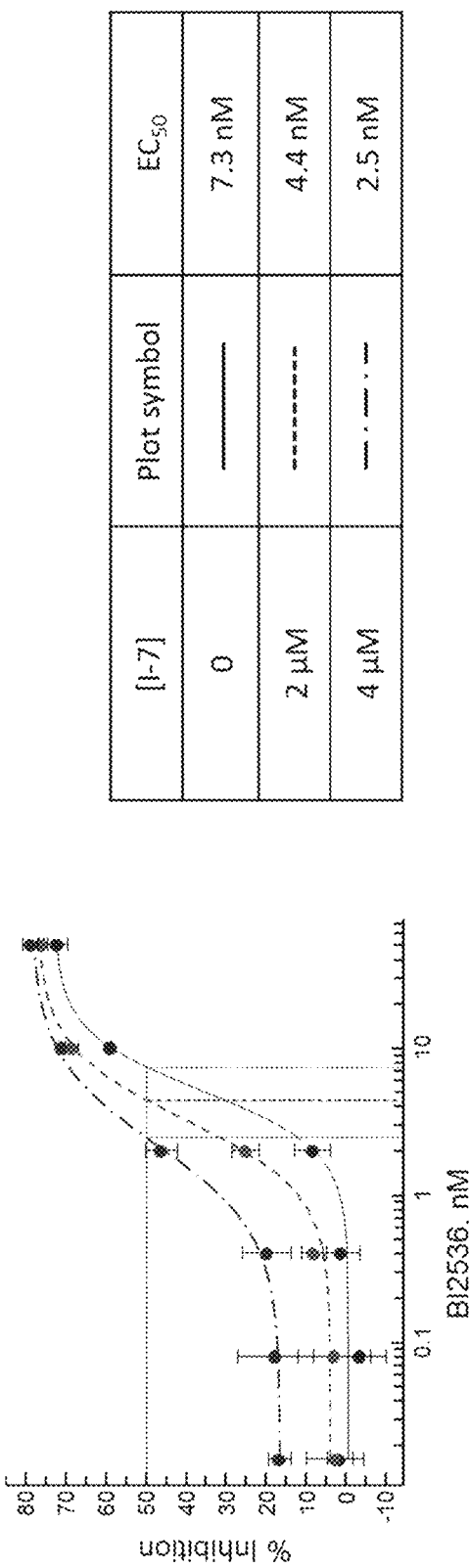
FIG. 26 shows effect of combination of B12536 and Compound I-7 (0, 2, and 4 µM) on the growth of PANC1 cells.

PANC1 cells were cultured, treated, and analyzed as described in Examples 1 and 2. The highest concentration of BI2536 used in this assay was 50 nM and the concentrations of Compound I-7 were 2 µM and 4 µM. The observed $EC_{50}$ values of BI2536 were 7.3 nM when Compound I-7 was not present, 4.4 nM when Compound I-7 was present at a concentration of 2 µM, and 2.5 nM when Compound I-7 was present at a concentration of 4 µM. See FIG. 26.

Figure 27:
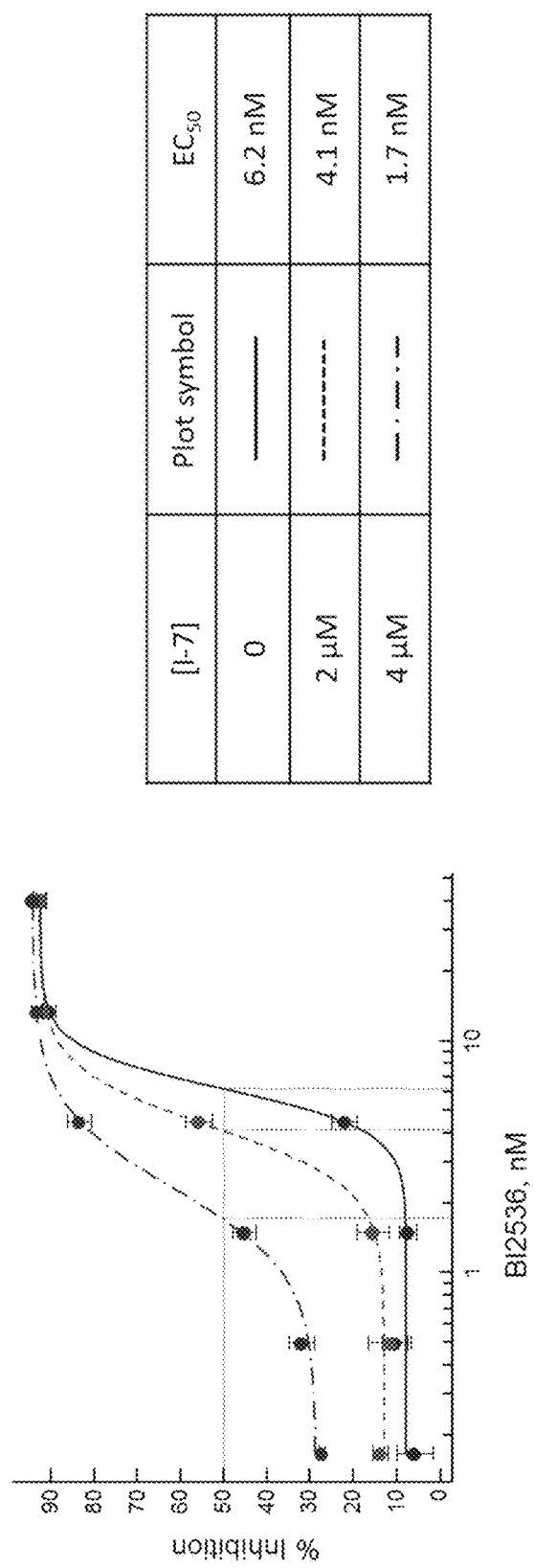
FIG. 27 shows effect of combination of B12536 and Compound I-7 (0, 2, and 4 µM) on the growth of DMS273 cells.

DMS273 cells were cultured, treated, and analyzed as described in Examples 1 and 2. The highest concentration of BI2536 used in this assay was 50 nM and the concentrations of Compound I-7 were 2 µM and 4 µM. The observed $EC_{50}$ values of BI2536 were 6.2 nM when Compound I-7 was not present, 4.1 nM when Compound I-7 was present at a concentration of 2 µM, and 1.7 nM when Compound I-7 was present at a concentration of 4 µM. See FIG. 27.

Figure 28:
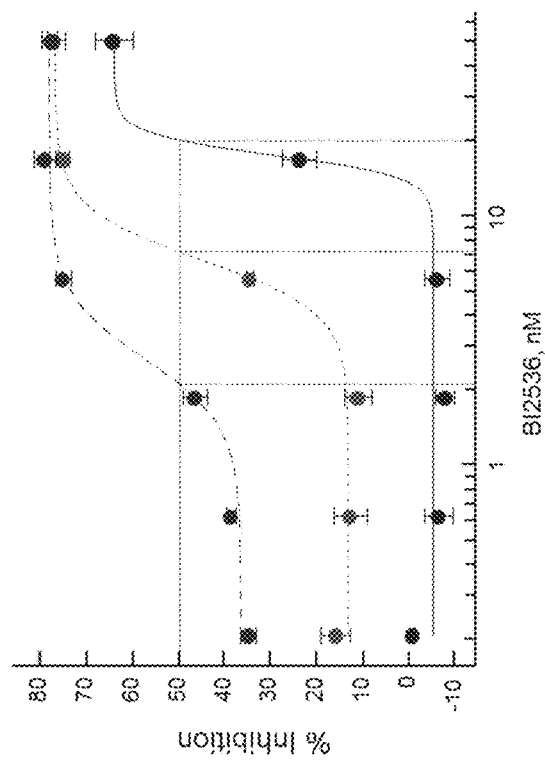
FIG. 28 shows effect of combination of B12536 and Compound I-7 (0, 2, and 4 µM) on the growth of A549 cells.

A549 cells were cultured, treated, and analyzed as described in Examples 1 and 2. The highest concentration of BI2536 used in this assay was 50 nM and the concentrations of Compound I-7 were 3 µM and 6 µM. The observed $EC_{50}$ values of BI2536 were 6.2 nM when Compound I-7 was not present, 4.1 nM when Compound I-7 was present at a concentration of 3 µM, and 1.7 nM when Compound I-7 was present at a concentration of 6 µM. See FIG. 28.

Example 8. Combination of a Molecule Effective Against Quiescent Cancer Cells with GSK461364

Figure 29:
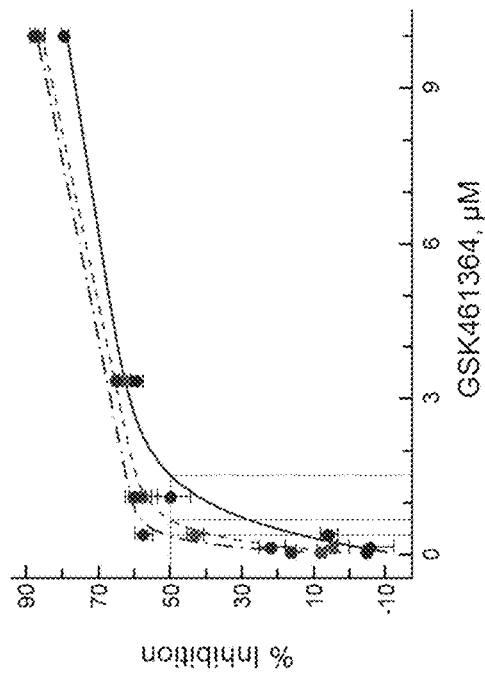
FIG. 29 shows effect of combination of GSK461364 and Compound I-7 (0, 2, and 4 µM) on the growth of H1975 cells.

H1975 cells were cultured, treated, and analyzed as described in Examples 1 and 2. The highest concentration of GSK461364 used in this assay was 10 µM and the concentrations of Compound I-7 were 2 µM and 4 µM. The observed $EC_{50}$ values of GSK461364 were 1.9 µM when Compound I-7 was not present, 0.97 µM when Compound I-7 was present at a concentration of 2 µM, and 0.58 µM when Compound I-7 was present at a concentration of 4 µM. See FIG. 29.

Figure 30:
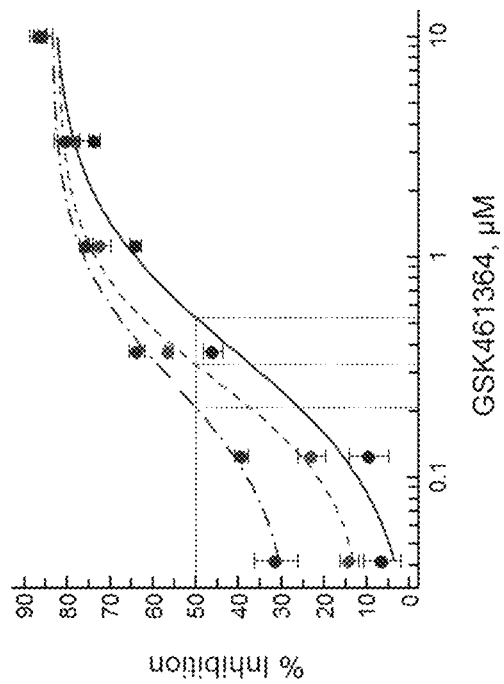
FIG. 30 shows effect of combination of GSK461364 and Compound I-7 (0, 2, and 4 µM) on the growth of PANC1 cells.

PANC1 cells were cultured, treated, and analyzed as described in Examples 1 and 2. The highest concentration of GSK461364 used in this assay was 10 µM and the concentrations of Compound I-7 were 2 µM and 4 µM. The observed $EC_{50}$ values of GSK461364 were 0.5 µM when Compound I-7 was not present, 0.3 µM when Compound I-7 was present at a concentration of 2 µM, and 0.2 µM when Compound I-7 was present at a concentration of 4 µM. See FIG. 30.

Figure 31:
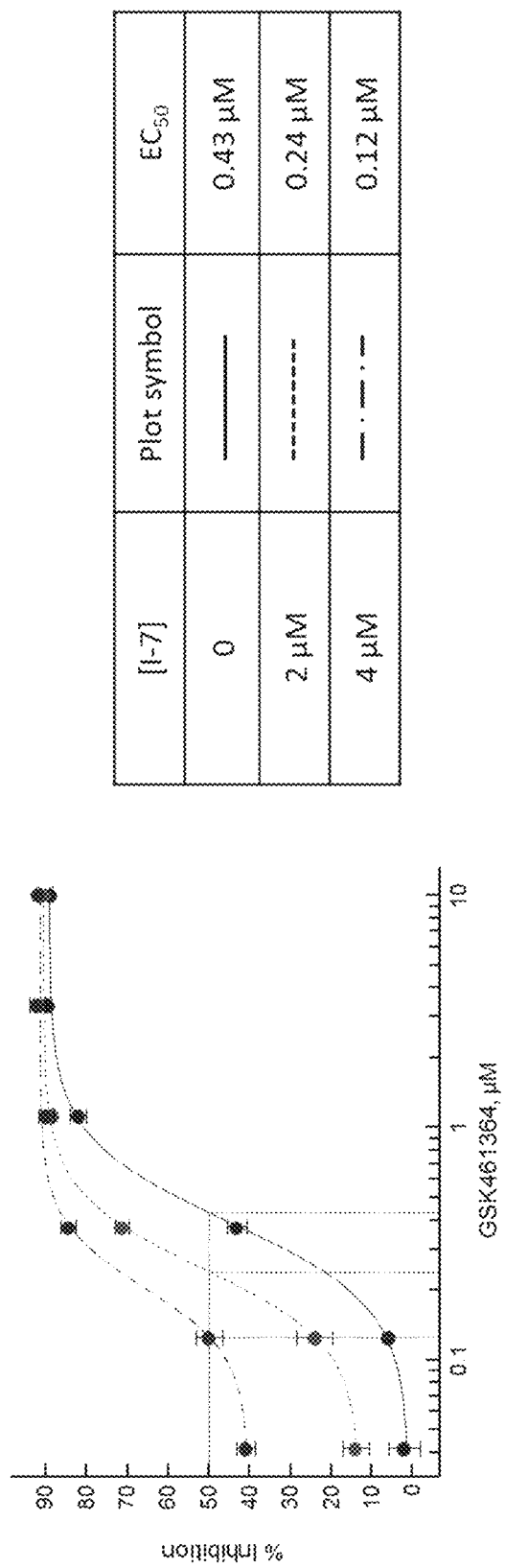
FIG. 31 shows effect of combination of GSK461364 and Compound I-7 (0, 2, and 4 µM) on the growth of DMS273 cells.

DMS273 cells were cultured, treated, and analyzed as described in Examples 1 and 2. The highest concentration of GSK461364 used in this assay was 10 µM and the concentrations of Compound I-7 were 2 µM and 4 µM. The observed $EC_{50}$ values of GSK461364 were 0.43 µM when Compound I-7 was not present, 0.24 µM when Compound I-7 was present at a concentration of 2 µM, and 0.12 µM when Compound I-7 was present at a concentration of 4 µM. See FIG. 31.

Figure 32:
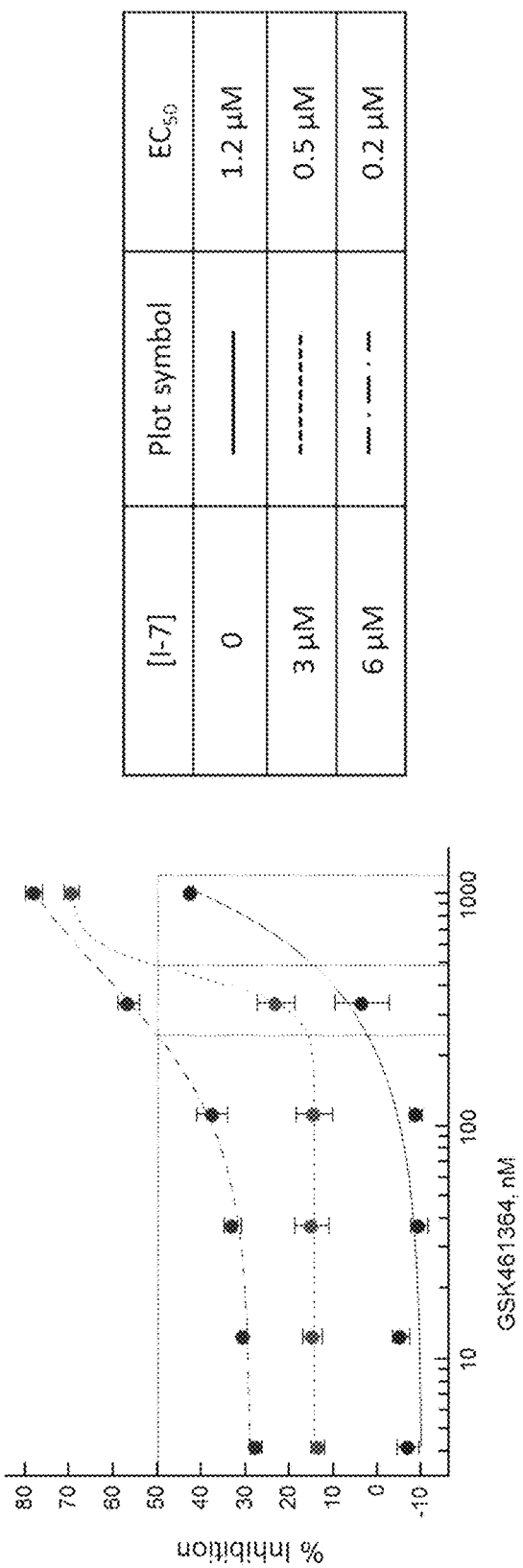
FIG. 32 shows effect of combination of GSK461364 and Compound I-7 (0, 3, and 6 µM) on the growth of A549 cells.

A549 cells were cultured, treated, and analyzed as described in Examples 1 and 2. The highest concentration of GSK461364 used in this assay was 1 µM and the concentrations of Compound I-7 were 3 µM and 6 µM. The observed $EC_{50}$ values of GSK461364 were 1.2 µM when Compound I-7 was not present, 0.5 µM when Compound I-7 was present at a concentration of 3 µM, and 0.2 µM when Compound I-7 was present at a concentration of 6 µM. See FIG. 32.

Figure 33:
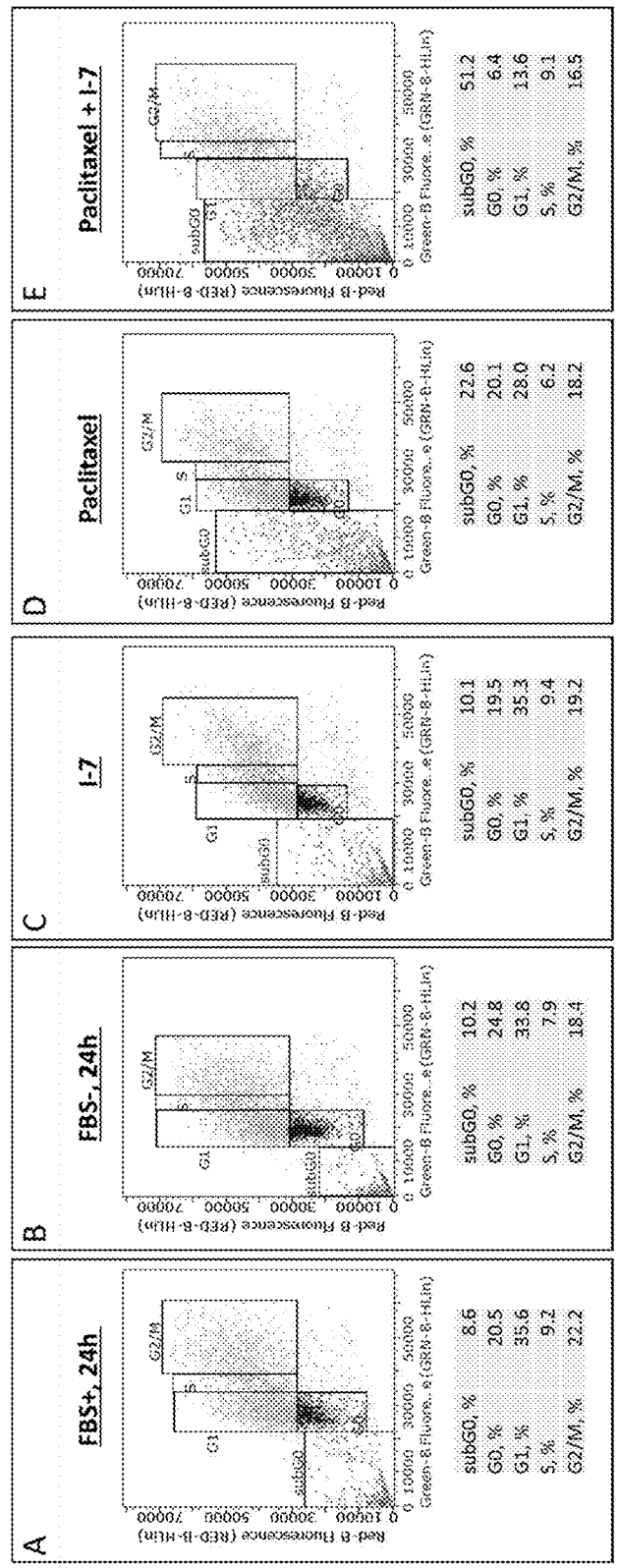
FIG. 33 shows FACS analyses of cell cycle distribution of DMS273 cells incubated for 24 hours in Panel A: FBS+ media; Panel B: FBS− media; Panel C: FBS+ media with 4 µM Compound I-7; Panel D: FBS+ media with 2.7 nM paclitaxel; Panel E: FBS+ media with 5 µM Compound I-7 and 2 nM paclitaxel.

Example 9. Cell Cycle Effects and Cytotoxicity of Paclitaxel and Combination of a Molecule Effective Against Quiescent Cancer Cells with Paclitaxel DMS273 cells were cultured, treated, and analyzed as described in Examples 1 and 2. The results when different concentrations of paclitaxel, Compound I-7, or both paclitaxel and Compound I-7 are present are shown in FIG. 33.

In this experiment it was demonstrated that exposure of DMS273 cells to paclitaxel does not result in pharmacological quiescence as the fraction of cells in $G_0$ phase of the cell cycle was similar with or without paclitaxel. It was also demonstrated that combination of Compound I-7 with paclitaxel strongly affected the cell cycle distribution of DMS273 cells and resulted in significant reduction of the fraction of cells in $G_0$. Moreover, the cytotoxicity of the combination was significantly higher than that of paclitaxel alone as evidenced by significant increases in fraction of apoptotic cells observed as sub-$G_0$ population.

The cell cycle distributions of normally proliferating DMS273 cells incubated in regular growth medium (FBS+) and DMS273 cells pre-incubated in serum free media (FBS−) are shown for comparison.

Figure 34:
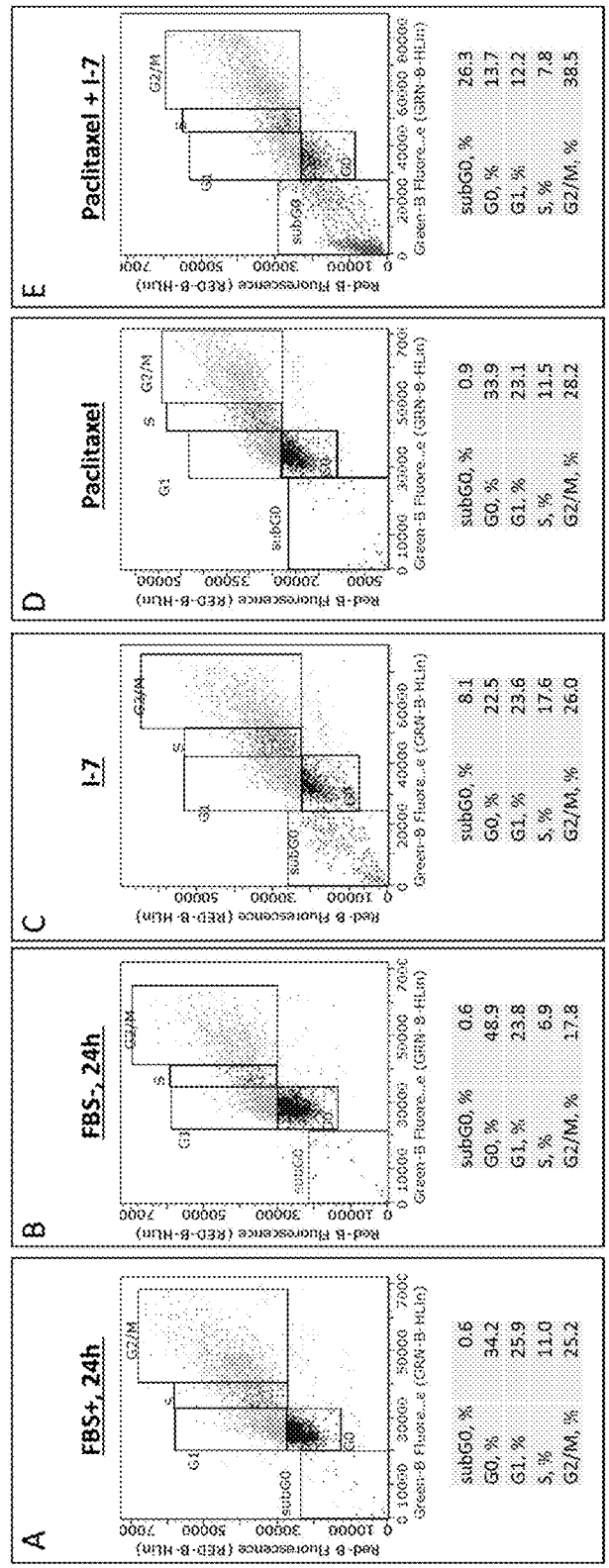
FIG. 34 shows FACS analyses of cell cycle distribution of SW620 cells incubated for 24 hours in Panel A: FBS+ media; Panel B: FBS− media; Panel C: FBS+ media with 4

SW620 cells were cultured, treated, and analyzed as described in Examples 1 and 2. The results when different concentrations of paclitaxel, Compound I-7, or both paclitaxel and Compound I-7 are present are shown in FIG. 34.

In this experiment it was demonstrated that exposure of SW620 cells to paclitaxel does not result in pharmacological quiescence as the fraction of cells in $G_0$ phase of the cell cycle was similar with or without paclitaxel in cells incubated in growth medium (FBS+). It was also demonstrated that combination of Compound I-7 with paclitaxel strongly affected the cell cycle distribution of SW620 cells and resulted in significant reduction of the fraction of cells in $G_0$. Moreover, the cytotoxicity of the combination was significantly higher than that of paclitaxel alone as evidenced by significant increases in fraction of apoptotic cells observed as sub-$G_0$ population.

The cell cycle distributions of normally proliferating SW620 cells incubated in regular growth medium (FBS+) and SW620 cells pre-incubated in serum free media (FBS−) are shown for comparison.

Example 10. Cell Cycle Effects and Cytotoxicity of Vincristine and Combination of a Molecule Effective Against Quiescent Cancer Cells with Vincristine DMS273 cells were cultured, treated, and analyzed as described in Examples 1 and 2. The results when different concentrations of vincristine, Compound I-7, or both vincristine and Compound I-7 are present are shown in FIG. 35.

In this experiment it was demonstrated that exposure of DMS273 cells to vincristine does not result in pharmacological quiescence as the fraction of cells in $G_0$ phase of the cell cycle was similar with or without vincristine in cells incubated in growth medium (FBS+). It was also demonstrated that combination of Compound I-7 with vincristine strongly affected the cell cycle distribution of DMS273 cells and resulted in significant reduction of the fraction of cells in $G_0$. Moreover, the cytotoxicity of the combination was significantly higher than that of vincristine alone as evidenced by significant increases in fraction of apoptotic cells observed as sub-$G_0$ population.

The cell cycle distributions of normally proliferating DMS273 cells incubated in regular growth medium (FBS+) and DMS273 cells pre-incubated in serum free media (FBS−) are shown for comparison.

Example 11. Cell Cycle Effects and Cytotoxicity of Vinorelbine and Combination of a Molecule Effective Against Quiescent Cancer Cells with Vinorelbine DMS273 cells were cultured, treated, and analyzed as described in Examples 1 and 2. The results when different concentrations of vinorelbine, Compound I-7, or both vinorelbine and Compound I-7 are present are shown in FIG. 36.

In this experiment it was demonstrated that exposure of DMS273 cells to vinorelbine does not result in pharmacological quiescence. It was also demonstrated that combination of Compound I-7 with vinorelbine affected the cell cycle distribution of DMS273 cells and resulted in significant reduction of the fraction of cells in $G_0$. Moreover, the cytotoxicity of the combination was significantly higher than that of vinorelbine alone as evidenced by significant increases in fraction of apoptotic cells observed as sub-$G_0$ population.

The cell cycle distributions of normally proliferating DMS273 cells incubated in regular growth medium (FBS+) and DMS273 cells pre-incubated in serum free media (FBS−) are shown for comparison.

Example 12. Cell Cycle Effects of AZ191 and Comparison with Compound I-7

The SW620 cells were cultured and treated as described in Example 1. For propidium iodide (PI) staining, manufacturer's protocol supplied with the Guava Cell Cycle Reagent for Flow Cytometry (EMD Millipore) was followed. The measurements were performed with Guava PCA-96 flow cytometer (EMD Millipore) using the green laser for excitation at 535 nm and monitoring emission at 617 nm.

The results when different concentrations of AZ191 were present are shown in FIG. 37. The data are average of two replicates.

The SW620 cells were cultured, treated, and analyzed as described in Examples 1. For propidium iodide (PI) staining, manufacturer's protocol supplied with the Guava Cell Cycle Reagent for Flow Cytometry (EMD Millipore) was followed. The measurements were performed with Guava PCA-96 flow cytometer (EMD Millipore) using the green laser for excitation at 535 nm and monitoring emission at 617 nm.

The results when different concentrations of Compound I-7 were present are shown in FIG. 38. The data are average of two replicates.

In these experiments, SW620 cells were incubated for 24 hours in FBS− media, which contained different concentrations of either AZ191 or Compound I-7. Under these conditions, exposure to AZ191 led to no decrease in fraction of cells in quiescent state ($G_0$) based on no observed change in the fraction of cells $G_0+G_1$ phase. Under the same conditions, exposure to same or lower concentrations of Compound I-7 led to a significant decrease in fraction of cells in quiescent state ($G_0$) based on the significant decrease in the fraction of cells $G_0+G_1$ phase.

AZ191 inhibits DYRK1B at 17 nM (Ashford A L, Oxley D, Kettle J, Hudson K, Guichard S, Cook S J, Lochhead P A (2014) A novel DYRK1B inhibitor AZ191 demonstrates that DYRK1B acts independently of GSK3beta to phosphorylate cyclin D1 at Thr(286), not Thr(288). Biochemical Journal 457, 43-56).

In this experiment, it was demonstrated that not all DYRK1 inhibitors are effective against quiescent cancer cells.

While this invention has been particularly shown and described with references to example embodiments thereof, it will be understood by those skilled in the art that various changes in form and details may be made therein without departing from the scope of the invention encompassed by the appended claims.

The invention claimed is:

1. A method for treating a subject having a neoplasm, the method comprising administering to the subject, sequentially or concomitantly, a DYRK1 inhibitor and administering to the subject an inhibitor of mitosis, wherein the DYRK1 inhibitor has a Formula I

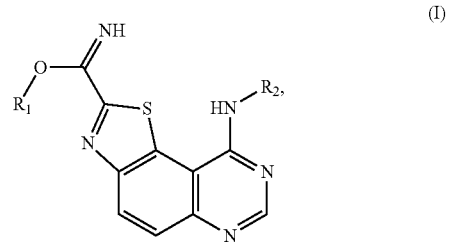

or a pharmaceutically acceptable salt or solvate thereof, wherein
$R_1$ is a substituted or unsubstituted $C_{1-8}$ alkyl, a substituted or unsubstituted phenyl, or a substituted or unsubstituted benzyl;
$R_2$ is phenyl, optionally substituted with up to four groups independently selected from halo, CN, $NO_2$, NHC(O) $C_{1-4}$ alkyl, $C_{1-4}$ alkyl, OH, $OC_{1-4}$ alkyl,
wherein two adjacent groups and their intervening carbon atoms may form a 5- to 6-membered ring containing one or more heteroatoms selected from N, O, or S.

2. The method of claim 1, further comprising administering to the subject an effective amount of radiation therapy.

3. The method of claim 1, wherein the neoplasm being treated is either a primary or metastatic cancer selected from biliary cancer, brain cancer, breast cancer, cervical cancer, colon cancer, gastric cancer, kidney cancer, head and neck cancer, leukemia, liver cancer, lung cancer, lymphoma, ovarian cancer, pancreatic cancer, prostate cancer, rectal cancer, sarcoma, skin cancer, testicular cancer, thyroid cancer, uterine cancer, bladder cancer, breast cancer, colorectal cancer, ovarian cancer, and prostate cancer.

4. The method of claim 1, wherein the neoplasm being treated is either a primary or metastatic cancer selected from colon cancer, non-small cell lung cancer, ovarian cancer, prostate cancer, small cell lung cancer, and pancreatic cancer.

5. The method of claim 1, wherein the inhibitor of mitosis is a taxane, a vinca alkaloid, or a PLK1 inhibitor.

6. The method of claim 1, wherein the inhibitor of mitosis is selected from BMS-188796, BMS-188797, cabazitaxel, DEP cabazitaxel, docetaxel, larotaxel (XRP9881, RPR109881), paclitaxel, taxoprexin (DHA-paclitaxel), and tesetaxel (DJ-927).

7. The method of claim 1, wherein the inhibitor of mitosis is selected from vinblastine, vincristine, vindesine, vinflunine, and vinorelbine.

8. The method of claim 1, wherein the inhibitor of mitosis is vintafolide.

9. The method of claim 1, wherein the inhibitor of mitosis is selected from BI-2536, GSK461364, GW843682X, HMN-214 and HMN-176, MLN-0905, NMS-P937, rigosertib, Ro3280, SBE 13, and volasertib.

10. The method of claim 1, wherein the DYRK1 inhibitor is selected from I-1, I-2, I-3, I-4, I-5, I-6, and I-7.

11. The method of claim 10, wherein inhibitor of mitosis is a taxane, a vinca alkaloid, or a PLK1 inhibitor.

12. The method of claim 10, further comprising administering to the subject an effective amount of radiation therapy.

13. The method of claim 10, wherein the inhibitor of mitosis is selected from BMS-188796, BMS-188797, cabazitaxel, DEP cabazitaxel, docetaxel, larotaxel (XRP9881, RPR109881), paclitaxel, taxoprexin (DHA-paclitaxel), and tesetaxel (DJ-927).

14. The method of claim 10, wherein the inhibitor of mitosis is selected from vinblastine, vincristine, vindesine, vinflunine, and vinorelbine.

15. The method of claim 10, wherein the inhibitor of mitosis is vintafolide.

16. The method of claim 10, wherein the inhibitor of mitosis is selected from BI-2536, GSK461364, GW843682X, HMN-214 and HMN-176, MLN-0905, NMS-P937, rigosertib, Ro3280, SBE 13, and volasertib.

17. The method of claim 10, wherein the neoplasm being treated is either a primary or metastatic cancer selected from biliary cancer, brain cancer, breast cancer, cervical cancer, colon cancer, gastric cancer, kidney cancer, head and neck cancer, leukemia, liver cancer, lung cancer, lymphoma, ovarian cancer, pancreatic cancer, prostate cancer, rectal cancer, sarcoma, skin cancer, testicular cancer, thyroid cancer, uterine cancer, bladder cancer, breast cancer, colorectal cancer, ovarian cancer, and prostate cancer.

18. The method of claim 10, wherein the neoplasm being treated is either a primary or metastatic cancer selected from colon cancer, non-small cell lung cancer, ovarian cancer, prostate cancer, small cell lung cancer, and pancreatic cancer.

19. A method for treating a subject having a neoplasm, the method comprising administering to the subject, sequentially or concomitantly,
(a) a DYRK1 inhibitor which inhibits DYRK1A or DYRK1B kinase activity with an $IC_{50}$ of 100 nM or lower in biochemical assays, and reduces the fraction of quiescent cancer cells (in vitro or in vivo) that would otherwise be found in the absence of such inhibitor by at least 10%; and
(b) administering to the subject an inhibitor of mitosis.

20. The method of claim 19, wherein the DYRK1 inhibitor has a Formula I

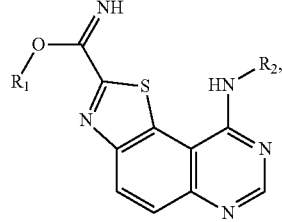

(I)

or a pharmaceutically acceptable salt or solvate thereof, wherein
$R_1$ is a substituted or unsubstituted $C_{1-8}$ alkyl, a substituted or unsubstituted phenyl, or a substituted or unsubstituted benzyl;
$R_2$ is phenyl, optionally substituted with up to four groups independently selected from halo, CN, $NO_2$, NHC(O) $C_{1-4}$ alkyl, $C_{1-4}$ alkyl, OH, $OC_{1-4}$ alkyl,
wherein two adjacent groups and their intervening carbon atoms may form a 5- to 6-membered ring containing one or more heteroatoms selected from N, O, or S.

* * * * *